(12) United States Patent
Kato et al.

(10) Patent No.: US 6,797,674 B2
(45) Date of Patent: Sep. 28, 2004

(54) SOLID AGRICULTURAL CHEMICALS COMPOSITION, PREPARATION THEREOF AND THE METHOD FOR SCATTERING THE SAME

(75) Inventors: Susumu Kato, Shizuoka (JP); Tetsuo Okawa, Shimizu (JP); Shigeki Fujita, Iwata (JP); Yoshihiro Maeda, Haibara-gun (JP)

(73) Assignee: Kumiai Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 10/066,560

(22) Filed: Feb. 6, 2002

(65) Prior Publication Data

US 2002/0155955 A1 Oct. 24, 2002

(30) Foreign Application Priority Data

Feb. 8, 2001 (JP) ..................................... 2001-032116

(51) Int. Cl.[7] .............................................. A01N 25/08
(52) U.S. Cl. ...................................... 504/367; 514/949
(58) Field of Search ........................... 504/367; 514/949

(56) References Cited

U.S. PATENT DOCUMENTS

| | | | | |
|---|---|---|---|---|
| 5,415,736 A | * | 5/1995 | Grether | ...................... 162/111 |
| 5,589,256 A | * | 12/1996 | Hansen et al. | ............... 428/283 |
| 6,207,729 B1 | * | 3/2001 | Medoff et al. | ............... 523/129 |
| 6,372,333 B1 | * | 4/2002 | Sugiyama et al. | ..... 428/311.71 |
| 6,486,095 B1 | | 11/2002 | Fujita et al. | ................ 504/367 |
| 6,528,569 B1 | * | 3/2003 | Oza et al. | ................... 524/442 |
| 2002/0098984 A1 | | 7/2002 | Fujita et al. | |

* cited by examiner

Primary Examiner—S. Mark Clardy
(74) Attorney, Agent, or Firm—Oblon, Spivak, McClelland, Maier & Neustadt, P.C.

(57) ABSTRACT

An object of the present invention is to provide a solid agricultural chemicals composition which is excellent in environmental safety, has no disadvantages of powdering and seeping out of an agrochemically active ingredient while containing the agrochemically active ingredient in high concentration and is excellent in residual-effect of the agriculturally active ingredient; a solid agricultural chemicals composition comprising a fragment of a fibre crop having high oil absorbency and a liquid agrochemically active ingredient at room temperature or liquid matter prepared by dissolving or dispersing an agrochemically active ingredient in a liquid solvent; and a method of producing the solid agricultural chemicals composition comprising the steps of impregnating a liquid agrochemically active ingredient at room temperature or liquid matter prepared by dissolving or dispersing the agrochemically active ingredient into a fragment of a fibre crop having high oil absorbency, and making it into a shape of powder, granule, or tablet.

16 Claims, 2 Drawing Sheets

Figure 1:
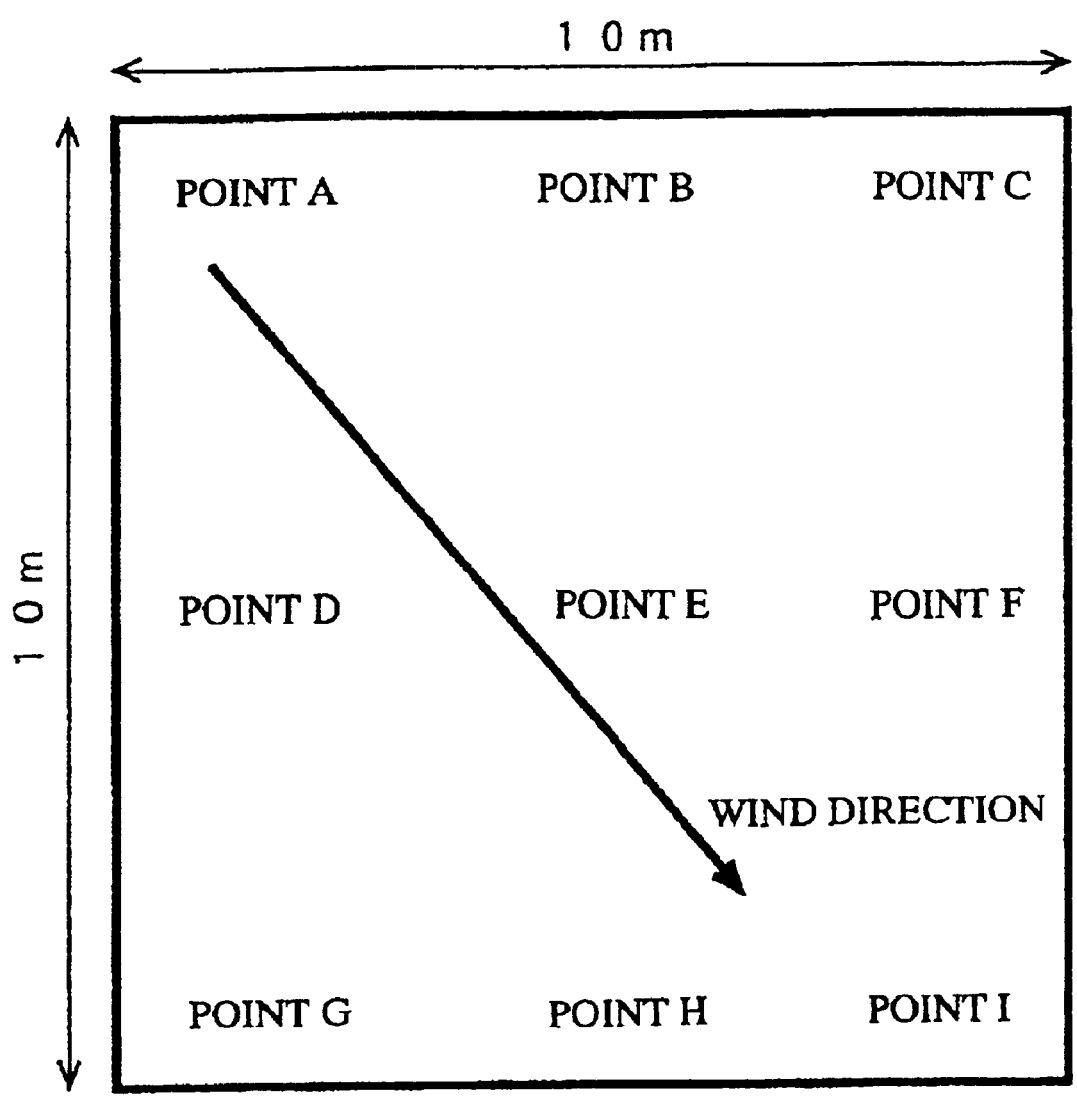
Figure 2:
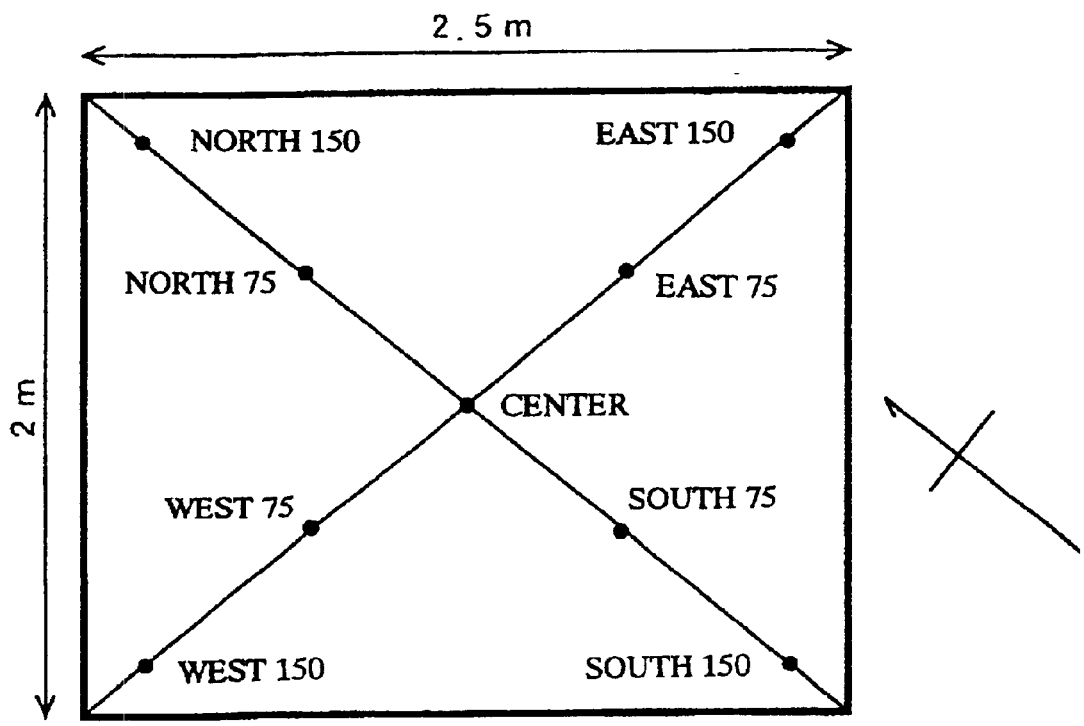

SOLID AGRICULTURAL CHEMICALS COMPOSITION, PREPARATION THEREOF AND THE METHOD FOR SCATTERING THE SAME

FIELD OF THE INVENTION

The present invention relates to a solid agricultural chemicals composition which uses a new carrier for agricultural chemicals, the preparation thereof and the method for scattering (applying) the same.

DESCRIPTION OF RELATED ART

At present, agricultural chemicals formulations are divided roughly into a solid chemicals formulation and a liquid chemicals formulation from its nature, and the former includes a dust type, a dust-granule mixture type, a granule type, a wettable powder type and so forth while the latter includes an emulsifiable type, a liquid type, a suspension type and so forth. In view of way of the application, they are classified into a direct scattering (applying) type and another type which is scattered (applied) after being diluted with water or the like.

On scattering (applying) an agricultural chemicals formulation, it is preferable for the agricultural chemicals to have preparatory processes for scattering (applying) as little as possible, and to be easy for scattering (applying) in view of the workability and the like. Considering the above circumstances, a solid chemicals formulation which can be scattered (applied) directly comes to be the most preferable agricultural chemicals formulation.

As such a solid chemicals formulation which can be scattered (applied) directly without dilution, a powder type such as a dust formulation, a DL (Drift Less) powder formulation, and a flowdust formulation, and a pellet type such as a granule type formulation, a fine granule type formulation F, a micro granule type formulation, and a micro granule type formulation F are known. Except the above, a jumbo type formulation in which a powder type formulation or a granule type formulation being packed with a water-soluble film, or tablets obtained by tablet molding, are thrown from a path between rice fields into a paddy field, a smoke type formulation which is used by firing a granular type formulation or a tablet type formulation with an ignition paper, a dust type formulation, a wettable powder type formulation, or a water dispersible granule type formulation which are mixed with soil to put in a box nursery of paddy rice are known.

However, since there are a liquid type at room temperature, a solid type at room temperature and a paste form whose melting point is near a room temperature, when classified according to nature of the agrochemically active ingredient in the agricultural chemicals formulation, it has been difficult to say that a solid chemicals formulation which contains an agrochemically active ingredient in high concentration and can be easily scattered (applied) directly can be obtained by using any agrochemically active ingredient.

That is, a liquid agrochemically active ingredient at room temperature can not be made a solid chemicals formulation by itself, and it is necessary to make it into a solid state with some means. In order to make a solid or paste-like agrochemically active ingredient at room temperature to be suitable for scattering (applying) directly, it is required to be dispersed uniformly in an agricultural chemicals formulation.

Therefore, on production of a solid chemicals formulation which can be scattered (applied) directly, a liquid agrochemically active ingredient at room temperature is kept as it is or is dissolved in an appropriate solvent, and then impregnated with a suitable carrier for agricultural chemicals, or a solid or paste-like agrochemically active ingredient at room temperature is liquidized with an appropriate solvent, and then impregnated with a suitable carrier for agricultural chemicals to obtain a solid chemicals formulation.

However, when an agrochemically active ingredient in high concentration is made into a solid chemicals formulation with a method described above, the agrochemically active ingredient in the chemicals formulation may possibly be pulverized according to the storage condition or due to changes with a lapse of time, or may seep out. Accordingly methods for preventing the above disadvantages are required.

On the other hand, if an agrochemically active ingredient contained in a solid chemicals formulation is soon released from the solid chemicals formulation which can be scattered (applied) directly, the concentration of the agricultural chemicals comes to be high in the vicinity of the chemicals formulation, and phytotoxicity may arise in some cases. Therefore, it is preferable for a solid agricultural chemicals formulation to release its agrochemically active ingredient gradually from the inside of the carrier, namely having a so-called residual-effectiveness.

Further, in recent years, safety of supplementary chemicals including carriers used for agricultural chemicals especially raises a new issue, and there have been strong demands for use of supplementary chemicals which are low in toxicity such as oral toxicity, dermal toxicity, inhalation toxicity, fish-toxicity, and eye irritation, and are excellent in biodegradability, and environmentally mild.

Incidentally, as a suitable carrier for agricultural chemicals to solidify an agrochemically active ingredient, conventionally, the following materials have been known, that is, clay, talc, diatmite, bentonite, calcium carbonate, silica, pumice, vermiculite, pearlite, Attapulgite clay, and so forth as a mineral carrier, fragment of soybean powder, tobacco powder, walnut powder, wheat flour, wood powder, rice bran, wheat bran, rice hull, sawdust, pulp flock, corn stem, nut skin, and fruit core and so forth as a vegetable carrier, and further synthetic carriers made from urea, ammonium sulfate, dextrin, white carbon and so forth.

Among them, as a carrier to be expected to solve the problems such as pulverization and seeping out of the agrochemically active ingredient, white carbon is widely used in an agricultural chemicals formulation due to its excellent oil absorbency. White carbon is called amorphous silica, and is synthetic silicate which is produced by means of a wet method or a dry method, and is used as an adsorptive carrier of liquid effective ingredients, an anti-caking agent for a solid chemicals formulation using an agrochemically active ingredient having a low melting point, and an auxilliary agent for pulverization when to be pulverized.

However, since white carbon is not biodegradability, which causes an environmental problem, and easily releases an active ingredient because it is fine in powder size, the effect of providing residual-effect can not be expected.

Among other oil-absorptive carriers, diatmite and bentonite as a mineral carrier are conceivable. However diatmite has a problem of being non-biodegradability, and bentonite has a problem in such that it restrains releasing of an agrochemically active ingredient too much due to its high adsorptivity, though it has no environmental problem because it is one of the main components of soil. On the other hand, vegetable carriers are susceptible to biodegradability, but they are all low in oil absorbency and water absorbency, so that they do not solve the problem associated with solidification of liquid agrochemically active ingredients.

A variety of studies has been made about chemicals formulation to give residual-effectiveness to an agrochemically active ingredient. For instance, a method of adding an anti-oxidation agent (Japanese Patent laid-open No. Hei 3-218304), a method of enclosing an active ingredient with a photo-degradative micro-capsule (Japanese Patent laid-open No. Sho 54-109078) and a method of pelletizing a solid agrochemically active ingredient having a melting point of 50° C. or more with amorphous silica (Japanese Patent laid-open Hei 8-143402), are known.

However, among these patent applications described above, for instance, there is apprehension of toxicity and biodegradability of the anti-oxidant in Japanese Patent laid-open of Hei 3-218304. Further, in Japanese Patent laid-open Sho 54-109078, a large amount of organic solvent is used during production, and the organic solvent is removed by drying, which causes fear on worsening of working environment during production. Still further, in Japanese Patent laid-open No. Hei 8-143402, there is only a solid agrochemically active ingredient which is effective, which means to throw out a plenty of non-biodegradability white carbon into environment. Thus, the fact is that any agricultural chemicals formulation which satisfies imparting of residual-effectiveness under consideration of safety and biodegradability of agricultural chemicals carriers to be used has not been obtained yet.

SUMMARY OF THE INVENTION

Accordingly, an object of the present invention is to provide a solid agricultural chemicals composition which is excellent in safety for environment, contains an agrochemically active ingredient in high concentration regardless of its nature, has no problem in pulverization and seeping out of the agrochemically active ingredient, and is excellent in residual-effectiveness of the agrochemically active ingredient.

As a result of assiduous study to achieve the above-described object, the present inventors have found that usage of pulverized matter of a fibre crop having suitable porosity and being excellent in oil absorbency as a carrier to carry an agrochemically active ingredient, can prevent pulverization and seeping out of the agrochemically active ingredient due to storage conditions and changes with a lapse of time, can hold a large quantity of the agrochemically active ingredient, can give less drifting of chemicals when scattered (applied) in the air, can release the agrochemically active ingredient gradually after scattering (applying) to impart residual-effectiveness, and that the fibre crop itself as a carrier disappears while undergoing biodegradability. Based upon this finding, the inventors have accomplished the present invention.

That is, the present invention is to provide a solid agricultural chemicals composition comprising a fragment of a fibre crop which is high in oil absorbency and a liquid agrochemically active ingredient at room temperature or liquid matter which is made by dissolving or dispersing an agrochemically active ingredient in a liquid solvent.

Another object of the present invention is to provide a method of producing a solid agricultural chemicals composition in which a liquid agrochemically active ingredient at room temperature or a liquid matter which is made by dissolving or dispersing an agrochemically active ingredient in a liquid solvent is impregnated into fragments of a fibre crop having high oil absorbency and water absorbency to make it into a shape of powder, pellet or tablet.

Still another object of the present invention is to provide a carrier for an oil agricultural chemicals composition which comprises fragments of a fibre crop as an active ingredient having oil absorption capacity of 100 or more.

BRIEF DESCRIPTION OF THE DRAWINGS

FIG. 1 is a view showing a paddy field having an area of 10 m by 10 m, used in Test Example 5. In the drawing, the point E is an application point of a composition for a paddy field;

FIG. 2 is a plan view of a vinyl house having 2 m long and 2.5 m width at a height of 2 m, used in Test Example 7. A central portion is an application point of a smoking agent; and FIG. 3 is a view showing a paddy field having an area of 20 m by 50 m, used in Test Example 9.

DETAILED DESCRIPTION OF THE PREFERRED EMBODIMENTS

A method of production of the solid agricultural chemicals composition of the present invention comprises the steps of: impregnating a fragment of a fibre crop having high oil absorbency as a carrier with a liquid agrochemically active ingredient at room temperature or liquid matter which is made by dissolving or dispersing an agrochemically active ingredient in a liquid solvent, and making it into a shape of powder, pellet or tablet.

As the fragment of the fibre crop used as a carrier having high oil absorbency, a chopped, crushed or pulverized fibre crop having suitable porosity and being susceptible to appropriate biodegradability in the environment can be cited. Especially, a fibre crop using leaves and hulls or stems are preferable because a desirable particle-size distribution for an agricultural chemicals carrier can be widely obtained by respective processing of chopping, crushing, pulverizing and so forth.

As a fibre crop used for a raw material of the carrier, cotton, kapok, flax, hemp, ramie, bouma, jute, kenaf, rozeru, aramina, sunhemp, Manila hemp, sisal, magey, heneken, isutori, Mauritius hemp, New Zealand hemp, fique, coconut palm, Panama hat plant, mat rush, sichitoui, licorice, futoi, Chinese mat rush, osier, bamboo, kozo, paper bush, broom corn, chizeru, sponge-gourd, can be cited. Preferably a variety of hemps such as ramie, Manila hemp, sisal, jute, bouma, sunhemp, kenaf, hemp, flax and so forth are used, and more preferably kenaf is used.

Incidentally, a pulverization product of a stem portion from corn and the like is not preferable because there is fear of drifting of chemicals on scattering (applying) due to low oil absorbency and low in apparent specific gravity when made it into a chemicals formulation.

This kenaf is a plant belonging to the genus Confederate rose in Hollyhock family Hollyhock order as classified by plant taxonomy, and a main type is a so-called Cuban kenaf (*Hibiscus Cannabinus* Linn.) which is improved in China for the purpose of harvesting its fiber. But there exist a so-called Thai kenaf (*Hibiscus Sabdariffa* Linn.) which is also called rosel or mesta in Southeast Asia, and evergrade in the United State, which belongs to Cuban kenaf family, those of which may also be used. The seed of kenaf is used for food oil, animal feed, and so forth, the outer skin of the trunk (bast fiber) is used for a hemp bag, rope, raw material for a fishnet non-woven cloth, and so forth, the pulped fiber (bast) is used for raw material of Japanese paper, cigarette paper, and speaker corn paper and so forth, the ligneous fiber of the trunk is used for board and the like, the pulped fiber (lignin) is used for speciality paper and the like, and all the trunk fiber is used for substituted raw material for wood pulp, for general paper and for others.

In the present invention, when kenaf is used as a fibre crop, since fragment of the trunk is used, it is preferable to use Cuban kenaf family whose trunk has a large diameter and whose outer skin is easy to separate from a ligneous portion, though it is not limited to Cuban kenaf family. The fragment of the kenaf trunk is generally obtained by removing the outer skin (bast) of the harvested trunk with a skin peeler and the like to cut the trunk in an appropriate length; drying the trunk at room temperature or by heat drying; pulverizing with a powdering machine such as a cutter mill and the like; and screening the pulverized trunk with a sieve to obtain the fragment having a desired particle size, but the method to obtain the kenaf fragment is not limited to this method. Incidentally, the kenaf may be used after surface treatment of the kenaf surface with a water soluble polymer or oil soluble polymer.

The particle size of the fragment of the above-described fibre crop can be varied in accordance with a form of the chemicals formulation to be processed or its method of production. For instance, when it is used for fine particles of a dust type formulation, flowdust or the like, the particle size must be 0.2 mm or less, preferably 0.05 mm or less, and when it is used for an extruding granulation type formulation or smoking agent, the particle size must be 0.8 mm or less, preferably 0.2 mm or less. When it is used for a base composition for a granule type formulation, a fine granule type formulation, and a micro granule type formulation which are used to absorb a liquid component, it must be screened particles of 2 mm or less and preferably 0.5 mm or less. Further, when it is used for a jumbo type formulation to hold a liquefied ingredient using a liquid component, solvent, or the like, it should be screened particles of 20 mm or less, preferably 5 mm or less.

However, when there is a pulverizing process in the production processes of the chemicals formulation, even particles having more larger particle sizes can be used.

Further, the fragment of the above-described fibre crop has preferably 100 or more in oil absorption capacity measured according to the following method of oil absorption measurement, and more preferably 200 or more, and the most preferable value is 250 or more.

Method of Measurement for Oil Absorption Capacity

A sample material 100 g for an oil absorption capacity measurement is taken into an Erlenmeyer flask which has a capacity to allow the sample material to roll and flow easily in the flask, and dibutyl phthalate (DBP) is added to mix with the sample material while being dropped, and the weight of the added DBP just before coagulation of the sample material is observed to obtain the weight of DBP absorption per 100 g of the sample material as the oil absorption value (g/100 g). It should be noted that the sampling weight of the sample material to be measured can be determined, according to the necessity, in a range of 5 g to 100 g depending on its bulk specific gravity, and in such a case, from actually measured value of dropped DBP weight, the oil absorption value (g/100 g) can be obtained by calculating the oil absorption weight of DBP per 100 g of the sample material in relation to the sampling weight of the sample material to be measured.

On the other hand, in the present invention, for an agrochemically active ingredient used for formulation of a solid agricultural chemicals composition, it is not limited to special chemicals so far as it is generally used for an agricultural chemical, and any form of agricultural chemicals in a form of solid, paste, or liquid at room temperature can be used. Further, for the agrochemically active ingredient, any ingredient regardless of soluble or insoluble in water can be used. For instance, agrochemically active ingredient for any purpose such as for a herbicide, for a fungicide, for an insecticide, or for a plant growth regulator can be used.

Among the agrochemically active ingredient described above, the examples which can be cited in a liquid state at room temperature are a herbicide such as 2-methyl-4-chlorophenoxy-thioacetic acid-s-ethyl (phenothiol), S-(4-chlorbenzyl) N,N-diethylthiocarbamate (thiobencarb), S-(2-chlorobenzyl)-N,N-diethylcarbamate (orbencarb), S-benzyl=1,2-dimethlpropyl (ethyl)thiocarbamate (esprocarb), S-ethylhexahydro-1H-azepin-1-carbothioate (molinate), 2-chloro-2',6'-diethyl-N-(butoxymethyl) acetanilide (butachlor), 2-chloro-2',6'-diethyl-N-(2-propoxyethyl)acetanilide (pretilachlor), and ethyl 4-(4-chloro-o-tryloxy)butylate (MCPB-ethyl), a fungicide such as O,O-diisopropyl-S-benzylthiophosphate (IBP), O-ethyl-S,S-diphenyldithiophosiphate (EDDP), insecticide such as O,O-dimethyl-O-(3-methyl-4-nitrophenyl)thiophosphate (MEP), (2-isopropyl-4-methylpyrimidyl-6)-diethylthiophosphate (diazinon), dimethyldicarbethoxyethyldithiophosphate (malathion), O,O-dipropyl-O-4-methylthiophenylphosphate (propaphos), 2,3- dihydro-2,2-dimethyl-7-benzo[b]flanyl=N-dibutylaminothio-N-methylcarbamate (carbosulfan), ethyl=N-[2,3-dihydro-2,2-dimethylbenzoflan-7-yloxycarbonyl (methyl) aminothio]-N-isopropyl-.beta.-alanynate (benfuracarb), (RS)-.alpha.-cyano-3-phenoxybenzyl=(RS)-2,2-dichloro-1-(4-ethoxyphenyl)cyclopropane carboxylate (cyclopropthrin), O,O-dimethyl-O-[3-methyl-4-(methylthio)phenyl] thiophosphate (MPP), dimethylthiophosphorylphenyl-methylacetate (PAP), and so on.

As an example of a paste agrochemically active ingredient having a low melting point, a herbicide such as S-1-methyl-1-phenylethyl=piperidine-1-carbothioate (dimepiperate),
2-methylthio-4-ethylamino-6-(1,2-dimethylpropylamino)-s-triadine (dimethametryn),
n-butyl-(R)-2-[4-(2-fluoro-4-cyanophenoxy)phenoxy] propionate (cyhalofop-butyl),
S,S'-dimethyl=2-difluoromethyl-4-isobutyl-6-trifluoromethylpyridine-3,5-dicarbithioate (dithiopyl),
2,3-dihydro-3,3-dimethylbenzofuran-5-ilethansulfonate (benfuresate),
N-(1-ethylpropyl)-3,4-dimethyl-2,6-dinitroaniline (pendimethalin), an insecticide such as 2-secondary-butylphenyl-N-methylcarbamate (BPMC), 2-(4-ethoxyphenyl)-2-methylpropyl=3-phenoxybenzyl=ether (etofenprox) and so on can be cited.

Further, as an example of a solid agrochemically active ingredient, a herbicide such as 2,4,6,-trichlorphenyl-4'-nitrophenylether (CNP), .alpha.-(2-naphthoxy) propionanilide (naproanilide), 5-(2,4-dichlorophenoxy)-2-nitrobenzoate methyl (bifenox), O-3-tert-butylphenyl=6-methoxy-2-pyridyl (methyl)thiocarbamate (pyributicarb), (RS)-2-bromo-N-(.alpha.,.alpha.-dimethylbenzyl)-3,3-dimethylbutylamide (bromobuthyde), 2-benzothiazol-2-yloxy-N-methylacetanilide (mefenacet), 1-(.alpha.,.alpha.-dimethylbenzyl)-3-(paratryl)urea (daimuron), methyl=.alpha.-(4,6-dimethoxypyrimidine-2-ylcarbamoylsulfamoyl)-O-toluate (bensulfuron-methyl), 1-(2-cloroimidazo[1,2-a]pyridine-3-ylsulfonyl)-3-(4,6-dimethoxypyrimidine-2-yl)urea (imazosulflon), ethyl=5-(4,6-dimethoxypyrmidine-2-ylcarbamoylsulfamoyl)-1-methylpyrasol-4-carboxylate (pyrazosulfuron-ethyl), 2methythio-4,6-bis(ethylamino)-s-triazine (simetryne), 2-methylthio-4,6-bis (isopropylamino)-s-triazine (prometryn), 2,4-dichlorophenyl-3'-methoxy-4'-nitrophenylether (chlomethoxynil), 5-tert-butyl-3-(2,4-dichoro-5-isopropoxyphenl)-1,3,4-oxadiazorin-2-one (oxadiazon), 4-(2,4-dichlorobenzoyl)-1,3-dimethyl-5-pyrazoryl-p-toluensulfonate (pyrazolate), 2-[4-(2,4-dichlorobenzoyl)-1,3-dimethylpyrazole-5-yloxy] acetophenone (pyrazoxyfen), (RS)-2-(2,4-dichloro-m- tolyloxy)propionanilide (clomeprop), 2-[4-[2,4-dichloro-m-toluoyl]-1,3-dimethylpyrazole-5-yloxy]-4'-methylacetophenon (benzofenap), 2-chloro-N-(3-methoxy-2-thenyl)-2',6'-dimethylacetanilide (thenylchlor), 3-[1-(3,5-dichlorphenyl)-1-methylethyl]2,3-dihydro-6-methyl-5-phenyl-4H-1,3-oxazine-4-on e (oxaziclomefone), 3-(4-chloro-5-cyclopentyloxy-2flyorophenyl)-5-isopropyridene-1,3-oxazolidine-2,4-dione (pentoxazone), 1-(diethylcarbamoyl)-3-(2,4,6-trimethylphenylsulfonyl)-1,2,4-triazole (cafenstrole), N-{[(4,6-dimethoxypyrimidine-2-yl)aminocarbonyl]}-1-methyl-4-(2-methyl-2H-tetrazole-5-yl) (azimsulfuron), methyl2-[(4,6-dimethoxypyrimidine-2-yl)oxy]-6-[(E)-1-(methoxyimino) ethyl]benzoate (pyriminobac-methyl), 4-(2-chloro-phenyl)-5-oxo-4,5dihydro-tetrazole-1-carboxylic acidcyclohexyl-ethylamide (fentrazamide), 3-(3,4-dichlorophenyl-1-methoxy-1-methylurea (linuron) and so on, a fungicide such as 3'-isopropoxy-2-methylbenzanilide (mepronil), .alpha.,.alpha.,.alpha.-trifluoro-3'-isopropoxy-O-toluanilide (flutolanil), 3,4,5,6-tetrachloro-N-(2,3-dichlorophenyl) phthalamid acid (tecloftalam), 1-(4-chlorobenzyl)-1-cyclopentyl-3-pheny urea (pencycuron), 6-(3,5-dichloro-4-methylphenyl)-3(2H)-pyridazinone (diclomezin), methyl=N-(2-methoxyacetyl)-N-(2,6-xylyl)-DL-alaninate (metalaxyl), (E)-4-chloro-.alpha.,.alpha.,.alpha.-trifluoro-N-(1-imidazole-1-yl-2-propoxyethylidene)-o-tolu idine (triflumizole), [5-amino-2-methyl-6-(2,3,4,5,6-pentahydroxycyclohexycyloxy) tetrahydropylan-3-yl] amino-.alpha.-iminoacetic acid (kasugamycin), validamycin, 3-aryloxy-1,2-benzoisothiazole-1,1-dioxyd (probenazole), diisopropyl-1,3-dithiolan-2-ylidene-malonate (isoprothiolane), 5-methyl-1,2,4-triazoro[3,4-b] benzothiazole (tricyclazole), 1,2,5,6-tetrahydropylolo[3,2,1-ij]chinoline-4-one (pyroquilon), 5-ethyl-5,8-dibydro-8-oxo[1,3]dioxolo[4,5-g]chinoline-7-carboxylic acid (oxolinic acid), (Z)-2'-methylacetophenone=4,6-dimethylpyrimidin-2-ylhydrazone 4,5,6,7-tetrachlorophthalide (ferimzone), 3-(3,5-dichlorophenyl)-N-isopropyl-2,4-dioxoimidazolidine-1-carboxyamide (iprodione), and so on, insecticide such as 1-naphthyl-N-methylcarbamate (NAC), O,O-diethyl-O-(3-oxo-2-phenyl-2H-pyridadine-6-yl) phosphorothioate (pyridaphenthion), O,O-dimethyl-O-3,5,6-trichoro-2-pyridylphosphorothioate (chiorpyrifos-methyl), O,O-dimethyl-S-(N-methylcarbamoylmethyl) dithiophosphate (dimethoate), O,S-dimethyl-N-acetylphosphoroamidethioate (acephate), ethylparanitrophenylthiono bennzene phosphonate (EPN), 1,3-bis (carbamoylthio)-2-(N,N-dimthylamamino) propane hydrochloride (cartap), 5-dimetbylamino-1,2,3-trithian oxalate (thiocyclam), S,S'-2-dimetylamino trimethylene=di (benzenthiosulfonate) (bensultap), 2-tert-butylimino-3-isopropyl-5-phenyl-1,3,5,6 tetrahydro-2H-1,3,5-thiadiazine-4-one (buprofezin), and so on, and a PGR (plant growth regulator) such as 4'-chloro-2-(.alpha.-hydroxybenzyl) isonicotinanilide (inabenfide), (2RS, 3RS)-1-(4-chlorophenyl)-4,4-dimethyl-2-(1H-1,2,4-triazole-1-yl) pentane-3-ol (paclobutrazol), (E)-(S)-1-(4-chlorophenyl)-4,4-dimethyl-2-(1H-1,2,4-triazole-1-yl)penta-1-ene-3-ol (uniconazole) and so forth can be cited.

The above-described agrochemically active ingredients are only examples and not limited to these ingredients, and the agrochemically active ingredient can be used alone or as a mixture of two kinds or more.

The rate of formulation of an agrochemically active ingredient in a solid agricultural chemicals composition according to the present invention differs depending on its type of formulation and usage of the solid agricultural chemicals composition or type of the agrochemically active ingredient, and not limited. In general, however, an agrochemically active ingredient is formulated in the agricultural chemicals composition in the range of 0.1 parts by weight to 70 parts by weight, and preferably 0.1 parts by weight to 10 parts by weight for a dust type formulation, 5 parts by weight to 40 parts by weight for a flowdust type formulation, a micro granule type, a fine granule type, a granule type and a smoking agent, and 10 parts by weight to 70 parts by weight for a jumbo type formulation. The rate of formulation of a fragment of the fibre crop which serves as a carrier also differs depending on its type of formulation and usage of the solid agricultural chemicals composition or the particle diameter, the oil absorbency and so forth of the fragment of the fibre crop, and not limited, but it is formulated generally in the range of 1 part by weight to 95 parts by weight in the composition, and the rate of formulation of the fragment of the fibre crop in relation to 100 parts by weight of a liquid raw material such as a liquid agrochemically active ingredient contained in the solid agricultural chemicals composition is generally in the range of 10 parts by weight to 1000 parts by weight, preferably 20 parts by weight to 700 parts by weight, and more preferably 30 parts by weight to 500 parts by weight.

The production of the solid agricultural composition of the present invention can be carried out according to an ordinary process except use of the fragment of the above-described fibre crop as a carrier. For instance, the production can be carried out in such that a fragment of a fibre crop is mixed and impregnated with a liquid agrochemically active ingredient at room temperature, or liquid matter of a solid or paste-like agrochemically active ingredient at room temperature and thereafter, the impregnated product is formulated in an ordinary method. A mixer such as a nauta mixer, a homogenizer or the like, or a crusher or a pelletizer such as a hammer mill or a Dyno mill or the like can be used for the production.

In the production described above, when a solid or past-like agrochemically active ingredient at room temperature is used, or when uniform impregnation is required even when a liquid agrochemically active ingredient is used, it is necessary that the liquid agrochemically active ingredient is liquefied by dissolving or dispersing in an appropriate liquid solvent, and impregnated with the fragment of the fibre crop.

For the liquid solvent used for this purpose, a liquid solvent that does not react with an agrochemically active ingredient which serves as a solute is suitable, and can be properly selected for use from liquid solvents generally used for an agricultural chemicals formulation. As a concrete liquid solvent, for instance, phthalic acid ester, alkylnaphthalene, alkylpyrolidone, phenylxyrylethane, glycerine, alkylene glycol, xylene, kerosine can be cited first, and an organic solvent such as methane series hydrocarbon, fatty acid ester, polybasic acid and so forth, and water, and further, the above-described liquid agrochemically active ingredient at room temperature can be used as a substitute for the liquid solvent. These liquid solvents can be used as a mixture of two kinds or more. It should be noted that a liquid solvent which is low in toxity as far as possible and susceptible to biodegradability is suitable for the object of the present invention.

The content of formulation of these liquid solvents can be generally in the range of 5 parts by weight to 500 parts by weight for 100 parts by weight of the agrochemically active ingredient, and preferably 10 parts by weight to 200 parts by weight, and more preferably 20 parts by weight to 100 parts by weight.

Alternatively, a fibre crop is impregnated with a liquid agrochemically active ingredient at room temperature, or with liquid matter of a solid or paste-like agrochemically active ingredient at room temperature and after the liquid solvent is dried and removed if necessary, the fibre crop is chopped, crushed, or pulverized into pieces, and can be processed to respective formulations by an ordinary method of formulation. The above-described liquid solvent can be used for the liquid solvent to be used for this case.

In the solid agricultural chemicals composition of the present invention, a surfactant can be formulated, if necessary, to enhance the effect of the agrochemically active ingredient.

Surfactants usually used in an agricultural chemicals formulation can be cited as a surfactant to be used. For instance, nonionic surfactant such as polyethylene glycol higher fatty acid ester, polyoxyethylene alkylether, polyoxyethylene alkylarylether, polyoxyethylene arylphenylether, sorbitanmonoalkylate, acetylene alcohol, acetylene diol, and alkylene oxide additives thereof; anionic surfactant such as alkylaryl sulfonate, dialkyl sulfonate, lignin sulfonate, naphthalene sulfonate and its condensate, alkyl sulfate ester, alkyl phosphate ester, alkylarylsulfate ester, alkylaryl phosphate ester, polyoxyethylene alkylether sulfate ester, polyoxyethylene alkylarylether sulfate ester, polyoxyethylene arylphenylether sulfate ester, polycarboxylic acid type polymer surfactant; and further a silicone series or fluorine series surfactant can be cited. These surfactants can be used alone or as a mixture of two kinds or more.

The rate of these surfactants to be used in the formulation is not limited to any specific value, but generally from 0.1 parts by weight to 30 parts by weight for 100 parts by weight of the agricultural chemicals composition, preferably from 0.5 parts by weight to 20 parts by weight, more preferably from 2 parts by weight to 10 parts by weight.

Further, in the solid agricultural chemicals composition of the present invention, a supplementary additives such as a water soluble polymer, a physical property improvement agent, an active ingredient stabilizer, a filler, a colorant, a pigment, and an essence can be added other than the above-described each component. These supplementary additives may be solid or liquid in nature, or may be almost insoluble or soluble.

Concrete examples of the supplementary additives are not limited to any specific ones, but fine mineral particles such as clay, calcium carbonate, bentonite, talc, diatomite; organic or inorganic salt such as ammonium sulfate, ammonium bicarbonate, ammonium nitrate, ammonium chloride, potassium chloride, sodium sulfate, magnesium sulfate, sodium citrate, sodium carbonate, sodium hydrogen carbonate; organic acids such as citric acid, and succinic acid; sugar such as cane sugar, lactose, xanthan gum, starch, dextrine; urea, xanthan gum, calcium stearate, and white carbon can be cited.

When a chemicals formulation such as a jumbo type formulation or the like is produced, a drift control additive can be used to increase the drift index on the water surface. As examples of the drift control additives, a mineral substance such as pumice, vermiculite, pearlite, and so forth; a vegetable matter such as unhulled rice, sugar cane, rice straw, wheat straw, coconut, banana, bamboo, ditch reed, corn core, wood and so forth can be cited. Further, an inorganic floatable core such as expanded shirasu made of shirasu, filite made of calcined aluminosilicates, microbaloons which are made by expanding sodium silicate or borax, fly ash, ceramic hollow body, and so on; and an organic floatable core such as phenol microbaloon made by phenol resin, echo-sphere made of epoxy resin, polyurethane foam made from polyurethane, microsphere made of vinylidene chloride and acrylonitrile copolymer and so forth can be cited. Among them, microsphere is used in a state that it is generally diluted in five to ten times with water, calcium carbonate, titan oxide and so forth. The rate of these drift control additives to be used in the formulation is not limited but generally from 0.3 parts by weight to 30 parts by weight, preferably from 1 part by weight to 10 parts by weight, for 100 parts by weight of the agricultural chemicals composition.

When a solid agricultural chemicals composition of the present invention is processed into a formulation type of powder formulation such as a dust type formulation, a DL dust type formulation, a flowdust type formulation and so forth, a physical property improvement agent such as isopropylphosphate, tall oil fatty acid and so forth; a flocculent such as vegetable oil, liquid paraffin and so forth; and an active ingredient stabilizer, and so forth, if necessary, are added to the fragment of the fibre crop which holds the above-described agrochemically active ingredient, and a mineral fine powder such as clay, DL clay, calcium carbonate and so forth are mixed, then the mixture may be crushed by an impact type crusher and so forth.

Further, when a solid agricultural chemicals composition of the present invention is processed into a formulation type of a powder formulation such as a wettable type, a surfactant such as a dispersing agent, and a wetting-and-spreading agent, and a physical property improvement agent, an active ingredient stabilizer and so forth, if necessary, are added to the fragments of the fibre crop which holds the above-described agrochemically active ingredient, and a mineral fine powder such as clay, calcium carbonate, diatmite, talc, bentonite and so forth are mixed, then the mixture may be crushed by an impact type crusher and so forth.

Further, when a solid agricultural chemicals composition of the present invention is processed into a formulation type of a granule formulation such as a granule type formulation, a dust-granule mixture type formulation (a fine granule type formulation F, a micro granule type formulation, a micro granule type formulation F), the desired product can be obtained by classifying the fragments of the fibre crop which holds the above-described agrochemically active ingredient with a sieve having meshes for an appropriate particle size. Such a sieve having particle sizes in the ranges of 300 $\mu$m to 1700 $\mu$m for a granule type formulation generally, 180 $\mu$m to 710 $\mu$m for a fine granule type formulation F generally, 106 $\mu$m to 300 $\mu$m for a micro granule type formulation generally, and 63 $\mu$m to 212 $\mu$m for a micro granule type formulation F generally, is used. Another method of production except the above will be explained later.

When a solid agricultural chemicals composition of the present invention is processed into a formulation type of a granule formulation (including a granular hydrated type) of an extruding granulation type, a surfactant such as a wetting-and-spreading agent or a dispersing agent or the like, a binder such as enzyme denatured dextrin, polyvinyl alcohol, carboxymethyl cellulose and so forth, a physical property improvement agent such as sodium tripolyphosphate and the like, and an active ingredient stabilizer and the like, if necessary, are added to the fragments of the fibre crop which holds the above-described agrochemically active ingredient, and thus obtained product is crushed with an impact type crusher and the like as necessary, then mineral fine powder such as powder of clay, talc, diatmite, calcium carbonate, bentonite or others is mixed and kneaded with water. Then it is pelletized with an extrusion granulation machine from a screen having an appropriate particle size and thus obtained pellets are dried. Then the desired product can be obtained by classifying the above pellets with a suitable sieve. Usually, a sieve having a particle size described above is used.

When a solid agricultural chemicals composition of the present invention is processed into a granular smoking agent, an organic foaming agent such as azodicarbonamide, dinitropentamethylenetetramine, azobisisobutylonitril and so forth, a physical property adjusting agent such as nitroguanidine, melamine, dicyandianamide, urea, bentonite and so forth, are added to the fragments of the fibre crop which holds the above-described agrochemically active ingredient, and kneaded with water. Then it is pelletized with an extrusion granulation machine from a screen having an appropriate particle size, and thus obtained pellets are dried and classified with a sieve. The screen used for the extrusion has an aperture generally in the range of 0.6 mm to 2 mm, preferably 0.8 mm to 1.2 mm. Alternatively, the desired product can be obtained by drying while adding water in a fluidized-bed dryer, and classifying with a sieve having an appropriate particle size.

When a solid agricultural chemicals composition of the present invention is processed into a smoking agent in a tablet type, it is obtained by further tableting the pellet type product obtained by the above-described method under an appropriate pressure and in a suitable size with a tableting machine or a briquette machine and the like. The size of a tablet is from 5 g to 100 g, preferably from 10 g to 80 g, and more preferably from 30 g to 80

Furthermore, when it is processed into a jumbo type, it is sufficient to classify the fragments of the fibre crop which holds the above-described agrochemically active ingredient with a sieve having a mesh of appropriate particle size. In order to make the particle size uniform, a sieve in the range of 0.5 mm to 20 mm, preferably in the range of 2 mm to 5 mm is used in general. Further, the fragments of the fibre crop which holds the above-described agrochemically active ingredient is put into a mixer such as a nauta mixer or a ribbon mixer, and a drift control additive, a surfactant such as a wetting-and-spreading agent, a dispersing agent and the like, supplementary additives such as colorant and an active ingredient stabilizer and so forth are further added in the mixer to obtain the desired product. A desired excellent effect can be obtained by scattering (applying) thus obtained product directly with hands or with a ladle or others, but in order to further enhance the safety and the convenience of handling, it is suitable to wrap the jumbo type formulation with a sheet of water-soluble film or water-dispersible film.

Each formulation of the present invention including the jumbo type formulation can be wrapped in a sheet of water-soluble film or water-dispersible film to enhance the usability, if necessary. Film made of a substance which is rapidly soluble in water is suitable for the film to be used for this purpose. For instance, the preferable materials are polyvinyl alcohol, polyoxypolyalkyleneglycol, hydroxypropylcellulose, hydroxypropyl methylcellulose, methylcellulose, sodium carboxymethylcellulose, sodium polyacrylate, alginic acid, gelatin, purulan, soluble starch, paogen, water-soluble paper, water-dispersible paper, and so forth. The thickness of the film is not limited but it is in general in the range of 20 $\mu$m to 100 $\mu$m. Incidentally, it can be wrapped with water-soluble film of the same material or of different material in multiply as necessary.

When the solid agricultural chemicals composition of the present invention is wrapped in the above-described water-soluble film or water-dispersible film, generally the film sheet is bent to make a bag with paste or by heat sealing, and the chemicals composition is filled in the bag and then the bag is sealed by pasting or heat sealing the opening of the bag. For the working efficiency, more preferable materials for the film are thermoplastic resins such as polyvinyl alcohol and the like. The weight of thus obtained package is in the range of 10 g to 200 g per bag and preferably 20 g to 100 g.

The solid agricultural chemical composition of the present invention thus produced is scattered (applied) in the following method, but not limited to the method.

That is, a dust type formulation (including a DL dust type formulations), a granule type formulation, a dust-granule mixture type formulation (a micro granule type formulation, fine granule type formulation F, a micro granule type formulation F) are scattered (applied) on a submerged paddy field, farm, and non-farming area by hand, with a hand granule applicator, by a tractor, helicopter, air plane equipped with a knapsack type power applicator or a granule applicator mounted with a boom type blow head hose or a blow head from levee or the like. The amount of scattering (applying) is generally from 0.25 kg to 4 kg for a submerged paddy field, from 3 kg to 6 kg for a farm, and from 5 to 15 kg for a non-farming area per 10 are of area. Further, these formulations can be scattered (applied) to soil in a nursery box for paddy rice or in a nursery box where all transplanted young rice comes out. The amount of scattering (applying) for a nursery box is generally from 30 g to 100 g per box.

A flowdust type formulation is scattered (applied) by blowing the flowdust type formulation from an entrance of a house such as a glass house or a vinyl house toward the inside with a power blower or a knapsack type power applicator. The normal amount of scattering is generally from 0.3 kg to 0.4 kg per 10 are.

A jumbo type formulation is scattered (applied) by throwing directly into a submerged paddy field from a path between paddy fields by hand. The amount of scattering is generally from 2 bags to 20 bags, preferably from 5 bags to 10 bags per 10 are, wherein a bag contains the agricultural chemicals formulation in the range of 10 g to 100 g, preferably in the range of 20 g to 60 g. Alternatively, the content is thrown directly by hand or with a ladle or scattered (applied) by a knapsack type power applicator without wrapping the content.

Furthermore, when a smoking agent is in a tablet form, it is used by putting it on a suspended metal fittings or the like in a house such as a glass house or a vinyl house, and by firing an ignition paper. The amount of scattering (applying) is generally from 2 to 10 tablets, preferably from 4 to 6 tablets per 10 are, wherein one tablet contains the formulation in the range of 20 g to 100 g, preferably 30 g to 60 g. When a powder type formulation or granule type formulation is scattered (applied) with a non-heat type fogging machine, it can be applied in accordance with the amount and directions suitable for the scattering machine to be used.

EXAMPLE

The present invention will be explained in detail hereinafter referring to examples and test examples, but the present invention is not limited to these examples. Incidentally, a term "parts" indicates "parts by weight" in the following examples.

Example 1

DL Dust Type Formulation of a Fungicide and Insecticide for a Paddy Field

A suspension type liquid matter obtained by mixing 3 parts of IBP, 2 parts of BPMC, 0.3 parts of Kumiresu (manufactured by Nikka Fats & Oil Co., LTD), and 0.2 parts of tall oil fatty acid (manufactured by Harima Kasei Kogyo Co., LTD.) is mixed with 4.5 parts of fragment of a kenaf trunk portion (passed through a 0.3 mm mesh sieve). 30 parts of clay (manufactured by Miyaki Industry Co., LTD.) and 60 parts of DL clay (manufactured by Miyaki Industry Co., LTD.) are added to this mixture and they are mixed together and crushed with a hammer mill (manufactured by Fuji Paudal Co., LTD.) to obtain a DL dust type formulation having a composition of the present invention.

Example 2

Dust Type Formulation of Fungicide for a Nursery Box 40 parts of TPN 40% suspension (water suspension) type agent(manufactured by Kumiai Chemical Industry Co., LTD.), Trade name Daconil 1000: containing 16 parts as TPN) is mixed with 3 parts of polyvinyl alcohol (manufactured by Nippon Gohsei Chemical Industry Co., LTD.) and 90 parts of kenaf trunk fragment (passed through a 0.3 mm mesh sieve: water content=10%), and dried with a fluidized-bed spray granulation equipment (manufactured by Powrex Co., LTD.) while setting an inlet temperature at 80° C. to obtain kenaf fragment containing 16% of TPN impregnated. 25 parts of thus obtained kenaf fragment is mixed with 0.5 parts of isopropylphosphate (manufactured by The Nippon Chemical Industry Co., LTD.) and 74.5 parts of clay and crushed with a hammer mill (manufactured by Fuji Paudal Co., LTD.) to obtain a dust type formulation having a composition of the present invention.

Example 3

Granule Type Formulation of a Fungicide and Insecticide for a Paddy Field 1 part of sodium dodecylbenzene sulfonate, 2 parts of sodium lignin sulfonate (manufacture by Nippon Paper Industries Co., LTD.), 2 parts of sodium tripolyphosphate, 15 parts of kenaf stem fragment (passed through a 0.3 mm mesh sieve), 30 parts of bentonite (manufactured by Kunimine Industries Co., LTD.), 25 parts of talc (manufactured by Kunimine Industries Co., LTD.) and 25 parts of clay (manufactured by Miyaki Industry Co., LTD.) are mixed. After being kneaded with an appropriate amount of water, it is pelletized with a kneading type pelletizer (manufactured by Fuji Paudal Co., LTD.) equipped with a 1.2 mm screen. Then, thus obtained pellets are dried to have 2% or less of water content with a Midget dryer (manufactured by Fuji Paudal Co., LTD.) while setting the inlet temperature of 90° C., and vacant base pellets are obtained by classifying the pellet with metal sieves of 0.5 mm and 1.7 mm. 17 parts of IBP and 4 parts of diazinon are added to and absorbed by 79 parts of the vacant base pellets to obtain a granule type formulation having a composition of the present invention.

Example 4

Granule Type Formulation of Fungicide and Insecticide for a Nursery Box 4 parts of tricyclazole, 2 parts of lignin calcium sulfonate (manufactured by Nippon Paper Industries Co., LTD.), 2 parts of polyvinyl alcohol (manufactured by Nippon Gohsei Chemical Industry Co., LTD.), 7 parts of kenaf stem fragment (passed through a 0.2 mm mesh sieve), 30 parts of bentonite (manufactured by Kunimine Industries Co., LTD.), and 50 parts of calcium carbonate (manufactured by Kunimine Industries Co., LTD.), are mixed. After being kneaded with an appropriate amount of water, it is pelletized with a kneading type pelletizer (manufactured by Fuji Paudal Co., LTD.) equipped with a 0.8 mm screen. Then, thus obtained pellet is dried with a midget dryer (manufactured by Fuji Paudal Co., LTD.) while setting the inlet temperature at 90° C., and a base pellet is obtained by classifying the pellet with metal sieves of 0.5 mm and 1.4 mm. 5 parts of propaphos is added to 95 parts of the vacant base pellet to be adsorbed to obtain a granule type formulation having a composition of the present invention.

Example 5

1 kg/10 are Granule Type Formulation of Herbicide for a Paddy Field 4.5 parts of mefenacet, 1 part of dodecylbenzen sodiumsulfonate, 2 parts of enzyme denatured dextrin (manufactured by Nippon Starch Chemical Co., LTD.), 2 parts of sodium tripolyphosphate, 10 parts of kenaf stem fragment (passed through a 0.3 mm mesh sieve), 25 parts of bentonite (manufactured by Kunimine Industries Co., LTD.) and 33.6 parts of calcium carbonate (manufactured by Kunimine Industries Co., LTD.) are mixed. After being kneaded with an appropriate amount of water, it is pelletized with a extrudig granulation type pelletizer (manufactured by Fuji Paudal Co., LTD.) equipped with a 1.2 mm screen. Then, thus obtained pellets are dried with a midget dryer (manufactured by Fuji Powdal Co., LTD.) while setting the inlet temperature at 90° C., and vacant base pellets are obtained by classifying the pellet with metal sieves of 0.5 mm and 1.4 mm. A mixed solution of 15 parts of benthiocarb, 2.4 parts of MCPB-ethyl, and 4.5 parts of simetryne is added to 78.1 parts of the base pellet to be adsorbed to obtain 1 kg/10 are granule type formulation having a composition of the present invention.

Example 6

Fine Granule Type Formulation F for Dry Field Farming

Liquid matter obtained by dissolving 24 parts of benthiocarb, 2.4 parts of pendimethalin, and 3.6 parts of linuron with heat, is mixed with 70 parts of kenaf trunk fragment (passed through a 0.71 mm mesh sieve) by spraying to obtain a fine granule type formulation having a composition of the present invention.

Example 7

Jumbo Type Formulation of Fungicide and Insecticide for a Paddy Field 42.5 parts of IBP, 10 parts of diazinon, 4 parts of polyoxyethylene alkylphenylphosphate and 2 parts of dioctylsulfosuccinate are dissolved with heat to obtain liquid matter. This liquid matter is mixed with 41.5 parts of kenaf stem fragment (passed through a 2 to 5 mm mesh sieve) by spraying to obtain particulate matter. 60 g of thus obtained particulate matter is filled into a three-side seal bag (50 $\mu$m:8 cm×12 cm) made of water-soluble polyvinyl alcohol film (manufactured by Nippon Gohsei Chemical Industry Co., LTD.: Hi-selon S-400), and the inlet of the bag is tight-sealed with a heat-sealer (manufactured by Fuji Impulse Co., LTD.) to obtain a jumbo type formulation having a composition of the present invention.

Example 8

Jumbo Type Formulation of Herbicide for a Paddy Field 37.5 parts of thiobencarb, 6 parts of MCPB-ethyl, 11.3 parts of simetryne, 11.3 parts of mefenacet, 5 parts of isoparaffin, 1.7 parts of polyoxyethylenestyrylphenylether sulfonate, 0.5 parts of polyoxyethylene alkylphenyl sulfonate, and 1.7 parts of dialkylsulfosuccinate are mixed to obtain suspended liquid matter. Thus obtained suspended liquid matter (specific gravity 0.89) and 25 parts of kenaf fragment (passed through a 2 to 5 mm mesh sieve) are mixed to obtain 100 parts of particulate matter. 40 g of thus obtained particulates is packed into a three-side seal bag (50 $\mu$m:8 cm×12 cm) made of water-soluble polyvinyl alcohol film (manufactured by Nippon Gohsei Chemical Industry Co., LTD.: Hi-selon S-400), and the inlet of the bag is tight-sealed with a heat-sealer (manufactured by Fuji Impulse Co., LTD.) to obtain a jumbo type formulation having a composition of the present invention.

Example 9

Jumbo Type Formulation of Herbicide for a Paddy Field 50 parts of benthiocarb, 1.7 parts of bensulfuron-methyl, 15 parts of mefenacet, 2 parts of polyoxyethylenestyrylphenylether sulfonate, 1 part of polyoxyethylene alkylether sulfonate, 1 parts of dialkylsulfosuccinate and 0.1 parts of oil brown GR (manufactured by Morisita And Co., LTD.) are mixed to obtain suspended liquid matter. Thus obtained suspended liquid matter and 29.2 parts of kenaf pieces (passed through a 2 to 5 mm sieve) are mixed, and thus obtained particulate matter is packed into a water-soluble polyvinyl alcohol film bag at a rate of 30 g per bag, and is tightly sealed by heat-sealing to obtain an agricultural chemicals composition for a paddy field according to the present invention.

Example 10

Jumbo Type Formulation of Herbicide for a Paddy Field 6 parts of cyhalofop-butyl are dissolved in 25 parts of diisodecyl adipade, and 8.4 parts of cafenstrole, 9 parts of daimuron, 2 parts of bensulfuron-methyl, 3 parts of polyoxyethylenestyrylphenylether sulfonate, 1.6 part of polyoxyethylene alkylether sulfonate, 3 parts of lignin sulfonate and 10 parts of methan series hydrocarbon are mixed with obtained suspended liquid matter.

Meanwhile, 10 parts of polyvinyl alcohol (manufactured by Nippon Gohsei Chemical Industry Co., LTD.) are dissolved in 90 parts of water, mixed with 100 parts of kenaf trunk fragment (passed through a 2 to 5 mm mesh sieve: water content=10%), and dried with a fluidized-bed spray granulation equipment (manufactured by Powrex Co., LTD.) while setting an inlet temperature at 80° C. to obtain kenaf pieces treated with polyvinyl alcohol.

Particulate matter obtained by mixing 68 parts of the suspended liquid matter obtained above and 32 parts of kenaf pieces treated with polyvinyl alcohol is packed in a water-soluble polyvinyl alcohol film bag at a rate of 25 g per bag, and tightly sealed by heat-sealing to obtain an agricultural chemicals composition for a paddy field according to the present invention.

Example 11

Smoking Agent of Fungicide for Green House 15 parts of mepanipyrym, 20 parts of kenaf trunk fragment (passed through a 0.2 to 0.8 mm mesh sieve), 5 parts of melamine, 15 parts of azodicarbonamide, 1 parts of dodecylbenzenesulfonate, 2 parts of polyvinyl alcohol (manufactured by Nippon Gohsei Chemical Industry Co., LTD.), 10 parts of alpha-starch (manufactured by Nippon Starch Chemical Co., LTD.), and 32 parts of calcium carbonate (manufactured by Kunimine Industries Co., LTD.) are mixed, and the mixture is crushed with a hammer mill (manufactured by Fuji Paudal Co., LTD.). After being kneaded with an appropriate amount of water, it is pelletized with a kneading type pelletizer (manufactured by Fuji Paudal Co., LTD.) equipped with a screen having 3 mm of diameter. The pellets thus obtained are dried with a midget dryer (manufactured by Fuji Paudal Co., LTD.) while setting the inlet temperature at 60° C. to obtain a smoking agent having a composition of the present invention by classifying them with metal sieves of 1.7 mm and 5 mm meshes.

Example 12

DL Dust Formulation of Fungicide and Insecticide for a Paddy Field

Suspended liquid matter obtained by mixing 3 parts of IBP, 2 parts of BPMC, 0.3 parts of kumiresu (manufactured by Nikka Fats & Oil Co., LTD.) and 0.2 parts of tall oil fatty acid (manufactured by Harima Kasei Kogyo Co., LTD.) and 4.5 parts of ramie trunk fragment (passed through a 0.3 mm mesh sieve). After adding 30 parts of clay (manufactured by Miyaki Industry Co., LTD.) and 60 parts of DL clay (manufactured by Miiyaki Industry Co., LTD.) thereto, it is crushed with a hammer mill (manufactured by Fuji Paudal Co., LTD.) to obtain a DL dust type formulation having a composition of the present invention.

Example 13

Dust Type Formulation of Fungicide for a Nursery Box 40 parts of TPN 40% suspension (water suspension) type agent (manufactured by Kumiai Chemical Industry Co., Ltd.: trade name Daconil 1000:16 parts as TPN) is mixed with 3 parts of polyvinyl alcohol (manufactured by Nippon Gohsei Chemical Industry Co., LTD.) and 90 parts of sunhemp trunk fragment (passed through a 0.3 mm mesh sieve: water content=10%), and the mixture is dried in a fluidized-bed spray granulation equipment (manufactured by Powrex Co., LTD.) with setting the inlet temperature at 80° C. to obtain sunhemp pieces which is impregnated with and hold 16% of TPN. 0.5 parts of isopropylphosphate (manufactured by The Nippon Chemical Industry Co., LTD.) and 74.5 parts of clay are mixed with 25 parts of this sunhemp piece and the mixture is crushed with a hammer mill (manufactured by Fuji Paudal Co., LTD.) to obtain a dust type formulation having a composition of the present invention.

Example 14

Granule Type Formulation of Fungicide and Insecticide for a Paddy Field 1 part of sodium dodecylbenzenesulfonate, 2 parts of sodium ligninsulfonate (manufactured by Nippon Paper Industries Co., LTD.), 2 parts of sodium tripolyphosphate, 15 parts bouma stem fragment (passed through 0.3 mm shieve), 30 parts of bentonite (manufactured by Kunimine Industries Co., LTD.), 25 parts of talc (manufactured by Kunimine Industries Co., LTD.), and 25 parts of clay (manufactured by Miyaki Industry Co., LTD.) are mixed together. The mixture is kneaded with an appropriate amount of water, and then pelletized with a kneading type pelletizer (manufactured by Fuji Paudal Co., LTD.) equipped with a 1.2 mm screen. The pellets are dried to have 2% or less of water content with a midget dryer (manufactured by Fuji Paudal Co., LTD.) while setting the inlet temperature at 90° C., and then classified them with metal sieves of 0.5 mm and 1.7 mm meshes to obtain vacant base pellets. 17 parts of IBP and 4 parts of diazinon are added to and absorbed by 79 parts of the vacant base pellets to obtain a granule type formulation having a composition of the present invention.

Example 15

Jumbo Type Formulation of Fungicide and Insecticide for a Paddy Field 42.5 parts of IBP, 10 Parts of diazinon, 4 parts of polyoxyethylene alkylphenylphosphate, and 2 parts of dioctylsulfosuccinate are dissolved with heat to obtain liquid matter. The liquid matter is sprayed to mixed with 41.5 parts of jute stem fragment (passed through 2 to 5 mm mesh sieve) to obtain particulate matter. 60 g of the particulate matter is packed in a three-side seal bag (50 µm:8 cm×12 cm) made of water-soluble polyvinyl alcohol film (manufactured by Nippon Gohsei Chemical Industry Co., LTD.: Hi-selon S-400), and the inlet is tightly sealed with a heat sealer (manufactured by Fuji Impulse Co., LTD.) to obtain a jumbo type formulation having a composition of the present invention.

Example 16

Granule Type Formulation of Herbicide for a Paddy Field 50 parts of thiobencarb, 3 parts of polyoxyethylene styrilphenylether sulfonate, 2 parts of alkylbenzen calciumsulfonate, 5 parts of kerosine are mixed to obtain liquid matter. Thus obtained liquid matter and 40 parts of kenaf trunk fragment (passed through a 2 to 5 mm mesh sieve: water content=10%) are mixed to obtained an agricultural chemicals composition of the present invention for a paddy field. The weight of one pellet is 7.1 mg and the apparent specific gravity is 0.4.

Example 17

Flowdust Type Formulation of Fungicide for Green House 15 parts of mepanipirym 40% suspension (water suspension) type composition (manufactured by Kumiai Chemical Industry Co. LTD.: trade name Frupica flowable; 6 parts as mepanipirym: water content=36%) and 95 parts of kenaf stem fragment (passed through a 0.05 mm sieve: water content=8%) are mixed and dried in a fluidized-bed dryer till water content thereof comes to 3% to obtain a flowdust composition of the present invention.

Example 18

DL Dust Type Formulation of Plant Growth Regulator for a Paddy Field 2 parts calcium prohexadionate 5% suspension (water suspension) type agent (manufactured by Kumiai Chemical Industry Co., LTD.: trade name Karutime flowable; 0.1 parts as calcium prohexadionate: water content=50%) and 1 part of kenaf stem fragment (passed through a 0.3 mm mesh sieve) are mixed. 0.5 parts of kumiresu (manufactured by Nikka Fats & Oil Co., LTD.), 26.5 parts of clay (manufactured by Miyaki Industry Co., LTD.) and 70 parts of DL clay are added to the mixture and crushed with a hammer mill (manufactured by Fuji Paudal Co., LTD.) to obtain a DL dust type formulation having a composition of the present invention.

Comparison Example 1

DL Dust Type Formulation of Fungicide and Insecticide for a Paddy Field

Suspended liquid matter obtained by mixing 3 parts of IBP, 2 parts of BPMC, 0.3 parts of kumiresu (manufactured by Nikka Fats & Oil Co., LTD.) and 0.2 parts of tall oil fatty acid (manufactured by Harima Kasei Kogyo Co., LTD.) and 4.5 parts of white carbon (manufactured by Shionogi & Co. LTD.). After adding 30 parts of clay (manufactured by Miyaki Industry Co., LTD.) and 60 parts of DL clay (manufactured by Miyaki Industry Co., LTD.) thereto, it is crushed by a hammer mill (manufactured by Fuji Paudal Co., LTD.) to obtain a DL dust type formulation for the comparison.

Comparison Example 2

Dust Type Formulation of Fungicide and Insecticide for a Nursery Box 4 parts of TPN, 0.5 parts of white carbon (trade name Carplex #80: manufactured by Shionogi & Co., LTD.), 0.5 parts of isopropylphosphate (manufactured by The Nippon Chemical Industry Co., LTD.) and 95 parts of clay (manufactured by Miyaki Industry Co., LTD.) are added and mixed. The mixture is crushed with a hammer mill (manufactured by Fuji Paudal Co., LT.) to obtain a dust type formulation for the comparison.

Comparison Example 3

Granule Type Formulation of Fungicide and Insecticide for a Paddy Field 1 part of sodium dodecylbenzene sulfonate, 2 parts of sodium lignin sulfonate (manufacture by Nippon Paper Industries Co., LTD.), 2 parts of sodium tripolyphosphate, 15 parts of white carbon (Carplex #80: manufactured by Shionogi & Co., LTD.), 30 parts of bentonite (manufactured by Kunimine Industries Co., LTD.), 25 parts of talc (manufactured by Kunimine Industries Co., LTD.) and 25 parts of clay (manufactured by Miyaki Industry Co., LTD.) are mixed. After being kneaded with an appropriate amount of water, it is pelletized with an extruding granulation type pelletizer (manufactured by Fuji Paudal Co., LTD.) equipped with a 1.2 mm screen. Then, thus obtained pellets are dried to have 2% or less of water content with a midget dryer (manufactured by Fuji Paudal Co., LTD.) while setting the inlet temperature at 90° C., and vacant base pellets are obtained by classifying the pellet with metal sieves of 0.5 mm and 1.7 mm meshes. 17 parts of IBP and 4 parts of diazinon are added to and absorbed by 79 parts of the vacant base pellet to obtain a granule type formulation for the comparison.

Comparison Example 4

Granule Type Formulation of Fungicide and Insecticide for a Nursery Box 4 parts of tricyclazole, 2 parts of calcium lignin sulfonate (manufactured by Nippon Paper Industries Co., LTD.), 2 parts of polyvinyl alcohol (manufactured by Nippon Gohsei Chemical Industry Co., LTD.), 7 parts of white carbon (manufactured by Shionogi & Co., LTD.), 30 parts of bentonite (manufactured by Kunimine Industries Co., LTD.), and 50 parts of calcium carbonate (manufactured by Kunimine Industries Co., LTD.), are mixed. After being kneaded with an appropriate amount of water, it is pelletized with an extruding granulation type pelletizer (manufactured by Fuji Paudal Co., LTD.) equipped with a 0.8 mm screen. Then, thus obtained pellets are dried with a midget dryer (manufactured by Fuji Paudal Co., LTD.) while setting the inlet temperature at 90° C., and base pellets are obtained by classifying the pellets with metal sieves of 0.5 mm and 1.4 mm meshes. 5 parts of propaphos is added to and adsorbed by 95 parts of the vacant base pellet to obtain a granule type formulation for the comparison.

Comparison Example 5

1 kg/10 are Granule Type Formulation of Herbicide for a Paddy Field 4.5 parts of mefenacet, 1 part of dodecylbenzen sodiumsulfonate, 2 parts of enzyme denatured dextrin (manufactured by Nippon Starch Chemical Co., LTD.), 2 parts of sodium tripolyphosphate, 10 parts of white carbon (manufactured by Shionogi & Co., LTD.), 25 parts of bentonite (manufactured by Kunimine Chemical Industry Co., LTD.) and 33.6 parts of calcium carbonate (manufactured by Kunimine Chemical Industry Co., LTD.) are mixed. After being kneaded with an appropriate amount of water, it is pelletized with an extruding granulation type pelletizer (manufactured by Fuji Paudal Co., LTD.) equipped with 1.2 mm screen. Then, thus obtained pellets are dried with a midget dryer (manufactured by Fuji Paudal Co., LTD.) while setting the inlet temperature at 90° C., and vacant base pellets are obtained by classifying the pellet with metal sieves of 0.5 mm and 1.4 mm meshes. A mixed solution of 15 parts of benthiocarb, 2.4 parts of MCPB-ethyl, and 4.5 parts of simetryne is added to and adsorbed by 78.1 parts of the base pellet to obtain 1 kg/10 are granule type formulation for the comparison.

Comparison Example 6

1 kg/10 are Granule Type Formulation of Herbicide for a Paddy Field 0.5 parts of bensulfuron-methyl, 3 parts of mefenacet, 1 part of dodecylbenzen sodiumsulfonate, 2 parts of enzyme denatured dextrin (manufactured by Nippon Starch Chemical Co., LTD.), 2 parts of sodium tripolyphosphate, 10 parts of white carbon (manufactured by Shionogi & Co., LTD.), 25 parts of bentonite (manufactured by Kunimine Industries Co., LTD.) and 41.5 parts of calcium carbonate (manufactured by Kunimine Industries Co., LTD.) are mixed. After being kneaded with an appropriate amount of water, it is pelletized with an extruding granulation type pelletizer (manufactured by Fuji Paudal Co., LTD.) equipped with a 1.2 mm screen. Then, thus obtained pellets are dried with a Midget dryer (manufactured by Fuji Paudal Co., LTD.) while setting the inlet temperature at 90° C., and vacant base pellets are obtained by classifying the pellet with metal sieves of 0.5 mm and 1.4 mm meshes. 15 parts of benthiocarb is added to and adsorbed by 85 parts of the base pellet to obtain 1 kg/10 are granule type formulation for the comparison.

Comparison Example 7

1 kg/10 are Granule Type Composition of Herbicide for a Paddy Field 0.5 parts of bensulfuron-methyl, 4.5 parts of diamuron, 2.1 parts of cafenstrole, 1 part of dodecylbenzen sodiumsulfonate, 2 parts of sodium ligninsulfonate, 2 parts of sodium tripolyphosphate, 10 parts of white carbon (manufactured by Shionogi & Co., LTD.), 25 parts of bentonite (manufactured by Kunimine Industries Co., LTD.) and 37.9 parts of calcium carbonate (manufactured by Kunimine Industries Co. LTD.) are mixed. After being kneaded with an appropriate amount of water, it is pelletized with an extruding granulation type pelletizer (manufactured by Fuji Paudal Co., LTD.) equipped with 1.2 mm screen. Then, thus obtained pellets are dried with a midget dryer (manufactured by Fuji Paudal Co., LTD.) while setting the inlet temperature at 90° C., and vacant base pellets are obtained by classifying the pellet with metal sieves of 0.5 mm and 1.4 mm meshes. 1.5 parts of cyhalofop-butyl, 10 parts of tridecyl phthalate and 3.5 parts of iso-paraffin are added to and adsorbed by 85 parts of the base pellet to obtain 1 kg/10 are granule type formulation for the comparison.

Comparison Example 8

Smoking Agent of Fungicide for Green House 15 parts of mepanipirym, 20 parts of nitrocellulose, 5 parts of melamine, 15 parts of azodicarbonamide, 1 parts of dodecylbenzenesulfonate, 2 parts of polyvinyl alcohol (manufactured by Nippon Gohsei Chemical Industry Co., LTD.), 10 parts of alpha-starch (manufactured by Nippon Starch Chemical Co., LTD.), and 32 parts of calcium carbonate (manufactured by Kunimine Industries Co., LTD.) are mixed, and the mixture is crushed with a hammer mill (manufactured by Fuji Paudal Co., LTD.). After being kneaded with an appropriate amount of water, it is pelletized with a kneading type pelletizer (manufactured by Fuji Paudal Co., LTD.) equipped with a screen having 3 mm of diameter. The pellets thus obtained are further dried with a midget dryer (manufactured by Fuji Paudal Co., LTD.) while setting the inlet temperature at 60° C. to obtain a smoking agent for the comparison by classifying them with metal sieves of 1.7 mm and 5 mm meshes.

Comparison Example 9

Fine Granule Type F Formulation of Herbicide for Dry Field Farming

Liquid matter obtained by dissolving 8 parts of benthiocarb, 0.8 parts of pendimethaline, and 1.2 parts of linuron with heat, is mixed with 85 parts of quartz sand group (passed through a 0.71 mm mesh sieve: manufactured by Ishikawalite Industry Co., LTD.) by spraying, and 5 parts of white carbon (manufactured by Shionogi & Co., LTD.) is added to the mixture till the mixture gets fluidized to obtain a fine granule type formulation F for the comparison.

Comparison Example 10

Granule Type Formulation of Herbicide for a Paddy Field 10 parts of benthiocarb and 90 parts of attapulgite clay (Tru-sorb #15/30) are mixed to obtain a granule type formulation for the comparison. The weight of one pellet is 0.7 mg and the apparent specific gravity is 0.7.

Comparison Example 11

Granule Type Formulation of Herbicide for a Paddy Field 10 parts of benthiocarb, 0.6 parts of polyoxyethylene styrilphenylether sulfonate, 0.4 parts of alkylbenzen calciumsulfonate, 1 part of kerosine are mixed to obtain liquid matter. Thus obtained liquid matter and 88 parts of crushed pieces of corn stem (passed through a 1 to 3 mm mesh sieve: water content=12%) are mixed to obtained a granule type formulation for the comparison. The weight of one pellet is 1.6 mg and the apparent specific gravity is 0.3.

Test Example 1

Effect Test of the DL Dust Type Formulation 4 roots of paddy rice (species: Kinmaze) are transplanted in a pot having an area of 200 cm$^2$. Two months later, the paddy rice is pruned at the height of 45 cm from the bottom of the pot, and the granule type formulation is scattered (applied) at a rate of 4 kg per 10 are, using a bell-jar dusting chamber having the bottom area of 1600 cm$^2$. After the application, it is kept outdoors on a bench with a roof and managed. Two pieces of a twig-and-leave portion are cut from the base portion on respective one, two, and four days after the application, and the lengths are adjusted to 17 cm, and they are put in test tubes having a diameter of 2 cm, a height of 20 cm, with 2 ml of water in it. Brown leafhoppers (Nilaparvata lugens: female imago) are released at a rate of 5 heads per unit area and kept controlled in a thermostatic chamber at 25° C. Two days and four days after releasing the insects, the death rate of the insects is investigated. The test is carried out in a six successive system and the average thereof is found. The DL dust type formulation in EXAMPLES 1, 12 and COMPARISON TEST 1 are used for the test. The result of the TEXT EXAMPLE 1 is shown in Table 1.

TABLE 1

| sample formulation | amount of chemicals treated (kg/10 a) | days after applying (releasing) | death rate of insect (%) | | |
|---|---|---|---|---|---|
| | | | on the day of the application | 2 days after the application | 4 days after the application |
| Example 1 | 4 | 2 days after | 97 | 87 | 57 |
| | | 4 days after | 100 | 97 | 83 |
| Example 12 | 4 | 2 days after | 100 | 83 | 73 |
| | | 4 days after | 100 | 97 | 87 |

TABLE 1-continued

| sample formulation | amount of chemicals treated (kg/10 a) | days after applying (releasing) | death rate of insect (%) | | |
|---|---|---|---|---|---|
| | | | on the day of the application | 2 days after the application | 4 days after the application |
| Comparison 1 | 4 | 2 days after | 97 | 23 | 3 |
| | | 4 days after | 100 | 40 | 10 |
| Non treatment area | 0 | 2 days after | 0 | 3 | 0 |
| | | 4 days after | 7 | 0 | 3 |

Test Example 2

Test for Effect of the Granule Type and Jumbo Type Formulation

Four roots of paddy rice (species: Kinmaze) are transplanted in a pot having an area of 500 cm$^2$. The granule type formulation is scattered (applied) 2 months later on the pot from the water surface at a rate of 4 kg and 2 kg per 10 are. After the application, it is kept outdoors on a bench with a roof and managed at the depth of water of 3 cm. Two pieces of a twig-and-leave portion are cut from the base portion respectively on the day of the application, 7 and 10 days after the application, and the length of the pieces is adjusted to 17 cm. Then they are put in test tubes having a diameter of 2 cm, a height of 20 cm, with 2 ml of water in it. Brown leafhoppers (*Nilaparvata lugens:* female imago) are released at a rate of 5 heads per unit area and kept controlled in a thermostatic chamber at 25° C. 2 days and 4 days after releasing the insects, the death rate of the insects is investigated. The test is carried out in 4 successive system per unit area and the average thereof is found. For the test, the granule type formulation in EXAMPLE 3 and EXAMPLE 14, Jumbo type formulation in EXAMPLE 7 and in EXAMPLE 15, and the granule type formulation in COMPARISON EXAMPLE 3 are used. The result of the TEXT EXAMPLE 2 is shown in Table 2.

transplanted at the transplantation depth of 2 cm and 10 days later, an adequate amount of the granule are scattered (applied) on the pot from the water surface. After the application, it is kept in a hothouse at a room temperature of 20° C. to 30° C. and managed at the water depth of 3 cm. 10 days, 30 days, and 50 days after the application of the chemicals formulation, the degree of phytotoxicity on the paddy rice is observed, comparing with that in the non treatment area, and 20 grains of early watergrass (*Echinochloa oryzoides* (ARD.) FRITSCH) and hotarui (*Scirpus juncoides* ROXB. var. *ohwianus* T. KOYAMA.) seeds are sown in the spot. 21 days after the sowing, the twig-and-leave portion is cut from the base portion and net weight of early watergrass is measured and found in comparison with that in the non-treatment area. The test is carried out in a six successive system per area and the average thereof is found. The granule type formulation in EXAMPLE 5, the jumbo type formulation in EXAMPLES 8 to EXAMPLE 10, and the granule type formulation in COMPARISON EXAMPLE 5 to COMPARISON EXAMPLE 7 are used for the test. As for the jumbo type formulation in EXAMPLE 8 to 10, contents of the chemicals formulation is used without wrapping it in a water-soluble film. The result of TEST EXAMPLE 3 is shown in Table 3.

TABLE 2

| sample formulation | amount of chemicals treated (kg/10 a) | days after applying (releasing) | death rate of insect (%) | | |
|---|---|---|---|---|---|
| | | | on the day of the application | 7 days after the application | 14 days after the application |
| Example 3 | 4 | 3 days after | 100 | 100 | 35 |
| | 2 | 3 days after | 95 | 85 | 30 |
| Example 7 | 4 | 3 days after | 100 | 100 | 75 |
| | 2 | 3 days after | 90 | 75 | 40 |
| Example 14 | 4 | 3 days after | 100 | 95 | 35 |
| | 2 | 3 days after | 90 | 80 | 15 |
| Example 15 | 4 | 3 days after | 100 | 95 | 70 |
| | 2 | 3 days after | 95 | 85 | 45 |
| Comparison 3 | 4 | 3 days after | 90 | 40 | 20 |
| | 2 | 3 days after | 55 | 15 | 10 |
| Non treatment area | 0 | 3 days after | 5 | 5 | 10 |

Test Example 3

Test for Effect of the Granule Type and Jumbo Type Formulation

Clay loam is filled in a 500 cm$^2$ Wagner pot, which is inlet-water and paddled, and kept for 2 days at 3 cm of the water depth. 4 roots of paddy rise (species: Kinmaze) are

TABLE 3

| sample formulation | amount of chemicals treated (kg/10 a) | day of sowing weeds | paddy rice | Echinochloa oryzoides (ARD.) FRITSCH | Scirpus juncoides ROXB. var. owianus T. KOYAMA |
|---|---|---|---|---|---|
| | | | | weight comparison with that in non treatment area (%) | |
| Example 5 | *1 | 10 days after | 98 | 0 | 1 |
| | | 30 days after | 99 | 6 | 4 |
| | | 50 days after | 101 | 5 | 3 |
| Example 8 | *1 | 10 days after | 97 | 0 | 1 |
| | | 30 days after | 98 | 7 | 1 |
| | | 50 days after | 101 | 3 | 5 |
| Comparison 5 | *1 | 10 days after | 97 | 5 | 2 |
| | | 30 days after | 97 | 11 | 14 |
| | | 50 days after | 93 | 51 | 38 |
| Example 9 | *2 | 10 days after | 103 | 0 | 2 |
| | | 30 days after | 99 | 2 | 4 |
| | | 50 days after | 101 | 6 | 3 |
| Comparison 6 | *2 | 10 days after | 103 | 4 | 2 |
| | | 30 days after | 99 | 9 | 11 |
| | | 50 days after | 101 | 48 | 37 |
| Example 10 | *3 | 10 days after | 103 | 1 | 2 |
| | | 30 days after | 99 | 5 | 9 |
| | | 50 days after | 101 | 6 | 3 |
| Comparison 7 | *3 | 10 days after | 101 | 13 | 11 |
| | | 30 days after | 99 | 13 | 9 |
| | | 50 days after | 101 | 39 | 44 |
| Non treatment area | 0 | 10 days after | 100 | 100 | 100 |
| | | 30 days after | 100 | 100 | 100 |
| | | 50 days after | 100 | 100 | 100 |

The amount of chemicals for treatment
*1: thiobencarb 150 g + mefenacet 45 g + MCPB-E 24 g + simetryne 45 g A.I./10 a
*2: thiobencarb 150 g + mefenacet 45 g + bensulfuron-methyl 5.1 g A.I./10 a
*3: cyhalofop-butyl 15 g + cafenstrole 21 g + dimron 22.5 g + bensulfuron-methyl 5 g A.I./10 a Test Example 4

Test for Effect of the Fine Granule Type Formulation F

Farm soil is filled in a 500 cm² container, and seeds of soybean (species: Hakucho) as a farm product, and seeds of slender amaranth (*Amaranthus viridis* L.) and southern crabgrass (*Digitaria adscendens* (H.B.K.) HENR.) as a weed are sown and they are mixed with soil at the depth of 2 cm. 1 day after the sowing, the fine granule type formulation F is scattered (applied) uniformly on the surface of the soil at an amount actually required and an amount corresponding to a half of that described above per 10 are. It is controlled to breed after scattering (applying) while keeping it on a bench with a roof along an alley. 10 days, 30 days, and 50 days after the scattering (applying), the degree of phytotoxicity on the farm product and the degree of growing of the weed are observed with naked eye, comparing with those in the non-treatment area. The test is carried out in a four successive system per unit area and the average thereof is found. The fine granule formulation F in EXAMPLE 6 and COMPARISON EXAMPLE 9 is used. The result of TEST EXAMPLE 4 is shown in Table 4.

TABLE 4

| sample formulation | amount of chemicals treated (kg/10 a) | day of sowing weeds | wheat | Amaranthus viridis L. | Digitaria adscendens (H.B.K.) HENR. |
|---|---|---|---|---|---|
| | | | | weight comparison with that in non treatment area % | |
| Example 6 | *1 | 10 days after | 98 | 0 | 1 |
| | | 30 days after | 99 | 6 | 4 |
| | | 50 days after | 101 | 8 | 3 |
| Example 6 | *2 | 10 days after | 97 | 0 | 1 |
| | | 30 days after | 98 | 5 | 6 |
| | | 50 days after | 101 | 6 | 4 |
| Comparison 9 | *1 | 10 days after | 98 | 8 | 9 |
| | | 30 days after | 99 | 22 | 26 |
| | | 50 days after | 101 | 33 | 38 |
| Comparison 9 | *2 | 10 days after | 97 | 19 | 26 |
| | | 30 days after | 98 | 35 | 46 |
| | | 50 days after | 101 | 78 | 66 |
| Non-treatment area | 0 | 10 days after | 100 | 100 | 100 |
| | | 30 days after | 100 | 100 | 100 |
| | | 50 days after | 100 | 100 | 100 |

The amount of chemicals for the application
*1: thiobencarb 400 g + pendimetharin 40 g + linuron 60 g A.I./10 a
*2: thiobencarb 200 g + pendimetharin 20 g + linuron 30 g A.I./10 a Test Example 5

Diffusion Property of Component in a Jumbo Type Formulation and Concentration of the Soil Surface Layer Jumbo type formulation is applied in an E point of a paddy field having 10 m×10 m in area shown in FIG. 1 and 5 cm in water depth. 24 hours after the application, water samples are withdrawn from respective points (A to I) shown in FIG. 1 and analyzed. The ratio of concentration of the agrochemically active ingredient obtained by analyzing the sample to the theoretical concentration when the agrochemically active ingredient is uniformly dispersed in the water is determined on the assumption that the above theoretical concentration would be 100%. Further, the coefficient of variation is calculated by dividing the standard deviation of the concentration in water in each point by mean value. The soil in each point in the extent of 10 cm in radius and 5 cm in depth is withdrawn with some water around the point after 24 hours from the application and is analyzed to obtain the ratio of concentration of the active ingredient of the agricultural chemicals obtained thus to the theoretical concentration when the agrochemically active ingredient is uniformly dispersed in the soil is determined on the assumption that the above theoretical concentration would be 100%. During the test, the water temperature is in the range of 18° C. to 24° C., and the wind is blowing at the velocity of 2 m to 4 m per second from the point A to the point I. The jumbo type formulation in EXAMPLE 9 is used for the test and the granule type formulation in COMPARISON EXAMPLE 6 which has the same application amount of the agrochemically active ingredient is used as the chemicals for the comparison. The result of TEST EXAMPLE 5 is shown in Table 5.

TABLE 5

| sample formulation | area point of sample collection | rate of concentration in water (%) | | | rate of concentration in soil (%) | | |
|---|---|---|---|---|---|---|---|
| | | thio-bencarb | bensulfouronmethyl | mefenacet | thio-bencarb | bensulfouronmethyl | mefenacet |
| Example 9 | A | 45 | 59 | 33 | 39 | 28 | 61 |
| | B | 51 | 66 | 38 | 41 | 27 | 66 |
| | C | 59 | 68 | 36 | 30 | 30 | 70 |
| | D | 53 | 61 | 41 | 29 | 33 | 71 |
| | E | 63 | 69 | 43 | 34 | 20 | 66 |
| | F | 65 | 80 | 53 | 39 | 25 | 67 |
| | G | 55 | 73 | 38 | 44 | 19 | 73 |
| | H | 62 | 78 | 49 | 43 | 25 | 59 |
| | I | 69 | 83 | 55 | 48 | 26 | 63 |
| | average | 58.0 | 70.8 | 42.9 | 38.6 | 25.9 | 66.2 |
| | deviation | 12.4 | 11.1 | 17.1 | 15.7 | 16.1 | 6.6 |
| Comparison 6 | A | 23 | 66 | 11 | 80 | 30 | 80 |
| | B | 26 | 63 | 15 | 75 | 18 | 88 |
| | C | 30 | 55 | 19 | 80 | 19 | 79 |
| | D | 19 | 69 | 13 | 83 | 25 | 78 |
| | E | 25 | 70 | 13 | 96 | 40 | 90 |
| | F | 22 | 53 | 16 | 79 | 27 | 71 |
| | G | 34 | 50 | 14 | 58 | 21 | 69 |
| | H | 28 | 59 | 19 | 89 | 38 | 92 |
| | I | 30 | 61 | 14 | 59 | 18 | 79 |
| | average | 26.3 | 60.7 | 14.9 | 77.7 | 26.2 | 80.7 |
| | deviation | 16.7 | 11.0 | 17.2 | 15.2 | 30.1 | 9.3 |

Test Example 6

Biological Test of Jumbo Type Formulation

In early May, paddy rice (species: Sasanishiki) is transplant in a paddy field having an area of 20 m×50 m, and 8 days later 10 pieces of jumbo type formulation in EXAMPLE 9 are thrown into the paddy field from a path between rice fields so that the jumbo type formulation is uniformly scattered (applied) on the field. It is observed that a water-soluble film which is used to wrap the composition started to dissolve after about 1 minute from the application, and the wrapped compositions were spreading while floating on the water surface without settling down into the bottom. On the day of the application, the wind was blowing at the velocity of 3 to 4 m per second. The jumbo type formulation in EXAMPLE 9 is used for the test, and the granule type formulation in COMPARISON EXAMPLE 6 which has the same application amount of the agrochemically active ingredient is used as the chemicals for the comparison. The result of TEST EXAMPLE 6 is shown in Table 6.

TABLE 6

| | | Effect of the chemicals | | | | | |
|---|---|---|---|---|---|---|---|
| sample formulation | area point of sample collection | phytotoxicity paddy rice | barnyard grass | *Scirpus juncoides* ROXB. var. *ohwianus* T. KOYAMA | *Monochoria vaginalis* PRESL var. *plantaginea* (ROXB.) | *Cyperus difformis* L. | *Sagittaria pygmaea* MIQ. |
| Example 9 | A | 0 | 10 | 9 | 10 | 10 | 9 |
| | B | 0 | 9 | 9 | 9 | 10 | 10 |
| | C | 0 | 10 | 10 | 10 | 10 | 9 |
| | D | 0 | 10 | 9 | 10 | 10 | 9 |
| | E | 0 | 9 | 10 | 10 | 10 | 9 |
| | F | 0 | 10 | 10 | 9 | 9 | 9 |
| | G | 1 | 10 | 10 | 9 | 9 | 9 |
| | H | 0 | 9 | 9 | 9 | 9 | 10 |
| | I | 1 | 10 | 10 | 10 | 10 | 10 |
| | J | 1 | 10 | 9 | 10 | 9 | 9 |
| | average | 0.3 | 9.6 | 9.5 | 9.5 | 9.6 | 9.3 |
| Comparison 6 | A | 0 | 9 | 8 | 9 | 9 | 8 |
| | B | 1 | 9 | 9 | 9 | 10 | 9 |
| | C | 1 | 9 | 9 | 9 | 9 | 9 |
| | D | 0 | 9 | 9 | 8 | 9 | 9 |
| | E | 0 | 9 | 9 | 9 | 9 | 9 |
| | F | 0 | 9 | 9 | 9 | 10 | 10 |
| | G | 0 | 9 | 9 | 9 | 9 | 9 |
| | H | 1 | 10 | 10 | 10 | 10 | 9 |
| | I | 1 | 10 | 10 | 10 | 10 | 10 |
| | J | 1 | 10 | 9 | 9 | 9 | 9 |
| | average | 0.5 | 9.3 | 9.1 | 9.2 | 9.4 | 9.1 |

Evaluation index: 10 = completely dead ~ 0 = no effect

Evaluation index: 10=completely dead~0=no effect

The result of examination of 9 points in the paddy field after 1 month from the application founds that weeds such as barnyard grass, hotarui (*Scirpus juncoides* ROXB. var. *ohwianus* T. KOYAMA), konagi (*Monochoria vaginalis* PRESL var. *plantaginea* (ROXB.)), smallflower umbrella sedge (*Cyperus difformis* L.), urikawa (*Sagittaria pygmaea* MIQ.) and so forth were observed in the paddy field where no agricultural chemicals was scattered (applied). However, no weed was observed, nor symptoms of phytotoxicity was observed in a paddy field where the jumbo type formulation for the paddy field of the present invention and the granule type formulation for comparison were uniformly scattered (applied).

Test Example 7

Diffusion Property Test of Component in the Smoking Agent

A suspended metal fittings (10 cm in height) with an ignition paper is provided in the central portion of a vinyl house (2 m long and 2.5 m width at a height of 2 m:10 m$^3$), and 0.6 g of a smoking agent is placed on the ignition paper. 10 pieces of bars having a piece of filter paper hung horizontally (the filter papers are placed at the height of 50 cm, 100 cm, and 150 cm) are placed along the diagonal lines at 0 cm, 75 cm, and 150 cm from the center. At 5 o'clock in the afternoon, the ignition paper is fired, and at 8 o'clock in the next morning (15 hours later), the filters are collected in each vinyl bag. 8 ml of acetonitril solution containing benzyl cinnamate as an internal standard substance is added into the vinyl bag to carry out extraction with shaking. Then, the extracted material is poured into a high pressure liquid chromatography equipped with a reverse-phase column to measure the material quantitatively. The smoking agent in EXAMPLE 11 and the smoking agent in COMPARISON EXAMPLE 8 are used in the test. The result of TEST EXAMPLE 7 is shown in Table 7.

TABLE 7

| sample formulation | area point of sample correction | amount of chemicals attached on the filter paper (ng/cm$^2$) | | |
|---|---|---|---|---|
| | | 50 cm | 100 cm | 150 cm |
| example 11 | 150 to the east | 837 | 803 | 850 |
| | 75 to the east | 899 | 906 | 912 |
| | 150 to the west | 850 | 874 | 898 |
| | 75 to the west | 901 | 905 | 914 |
| | 150 to the south | 861 | 835 | 884 |
| | 75 to the south | 905 | 898 | 902 |
| | 150 to the north | 900 | 904 | 911 |
| | 75 to the north | 920 | 930 | 925 |
| | center | 931 | 955 | 962 |
| | average | 889 | 890 | 906 |
| | variation | 3.42 | 4.94 | 3.15 |
| comparison 8 | 150 to the east | 755 | 799 | 735 |
| | 75 to the east | 833 | 966 | 963 |
| | 150 to the west | 768 | 886 | 914 |
| | 75 to the west | 845 | 906 | 895 |
| | 150 to the south | 848 | 890 | 894 |
| | 75 to the south | 807 | 896 | 956 |
| | 150 to the north | 811 | 905 | 883 |
| | 75 to the north | 861 | 900 | 946 |
| | center | 905 | 956 | 996 |
| | average | 826 | 900 | 909 |
| | variation | 5.32 | 4.98 | 7.82 |

Test Example 8

Application Test for Rice Blast Disease on a Nursery Box

Artificial ridging is filled in a nursery box (30×60×3 cm), and 180 g of seed rice (in terms of dried seed rice weight) per box (species: Aichi asahi) is sowed. 3 weeks after the sowing, the granule type formulations in EXAMPLE 4 and COMPARISON EXAMPLE 4 are applied uniformly on the nursery box so that the active ingredients come to a predetermined amount. 4 hours after the application, each 5 stems of the young rice plants are taken with the artificial ridging for breeding young rice, and transplanted onto a Wagner pot of 1/10000a. 30 days and 50 days after the application, conidiospore suspension of rice blast disease germ (*Pyricularia oryzae*) is sprayed and inoculated on the young rice plants, which are immediately put in a high humidity room at 25° C. for 24 hours. Then, they are transferred in a green house, and the number of morbid spots on a leaf which locates at the highest on the stem at the time of the inoculation is examined 5 days after the inoculation. A preventive value is found from the following formula and the result evaluated from criteria which will be described later is shown in Table 8.

preventive value (%) = [Formula 1]

$$\left(1 - \frac{\text{number of spots in treated area}}{\text{number of spots in non-treated area}}\right) \times 100$$

(Evaluation criteria)
Evaluation: contents
 A: 100% in preventive value
 B: Less than 100% to 80.0% or more in preventive value
 C: Less than 80.0% to 50.0% or more in preventive value
 D: Less than 50% in preventive value
(Result)

TABLE 8

| | | evaluation on value of prevention | |
|---|---|---|---|
| sample formulation | amount of chemicals applied (g/box) | 30 days after application | 50 days after application |
| Example 4 | 50 | A | B |
| | 25 | A | B |
| Comparison 4 | 50 | B | B |
| | 25 | B | C |

Test Example 9

Drift Test of Granule Type Formulation

Figure 3:
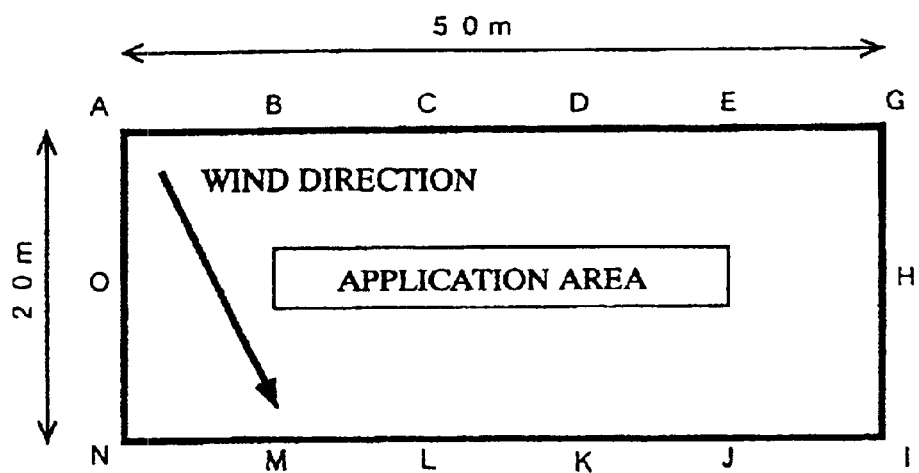

In early June, paddy rice (species: Koshihikari) is transplant in a paddy field having an area of 20 m×50 m shown in FIG. 3 and 5 cm in water depth. 5 days later, glass petri dishes (12 cm in diameter) are placed on a path around the paddy field at every 10 m from the corner, and 20 ml of water is poured in each dish so that it serves as a trap vessel for drifting of chemicals. Agricultural chemicals are filled in a tank for chemicals attached to a radio-controlled helicopter equipped with a granule applicator and scattered in the air on an area having a straight distance of 30 m between 10 m inside of the paddy field from a middle portion of the short side and 10 m back toward the inside from a middle portion of the opposite short side from a height of 3 m at the impeller revolution of 1300 rpm. Incidentally, on the day of the application, the wind was blowing at the velocity of 3 to 4 m per second from the point A toward the point M. The granule type formulation in EXAMPLE 16, COMPARISON EXAMPLE 10 and COMPARISON EXAMPLE 11 are used for the test. After the application, the composition of the present invention is observed to spread drifting on the water surface, while the granules of COMPARISON EXAMPLES are observed to sink in the bottom of water. After the application, the trap vessels for the drift are recovered and the content is analyzed by adding an acetone solution containing an internal standard thereto. The result of TEST EXAMPLE 9 is shown in Table 9. The paddy field is examined 1 month after the application, and barnyard grass which is the weed to be studied was observed in plenty amount around ridges between rice fields in the area where the granule type formulation to be compared is applied for the comparison, while little barnyard grass was observed in the whole paddy field where the granule type formulation of the present invention for a paddy field was applied, and no symptoms of phytotoxicity was observed.

TABLE 9

| sampling point | Amount of Drift ($\mu$g/cm$^2$) | | | | | | | | | | | | | | |
| --- | --- | --- | --- | --- | --- | --- | --- | --- | --- | --- | --- | --- | --- | --- | --- |
| | A | B | C | D | E | F | G | H | I | J | K | L | M | N | O |
| Example 16 | ND | ND | ND | ND | ND | ND | ND | ND | ND | ND | ND | ND | ND | ND | ND |
| Comparison 10 | ND | ND | 0.2 | ND | ND | ND | 0.2 | 0.7 | 2.8 | 4.1 | 3.3 | 1.9 | 0.4 | 0.1 | ND |
| Comparison 11 | ND | ND | ND | 0.5 | 0.2 | ND | ND | 1.2 | 4.5 | 5.6 | 6.2 | 3.5 | 1.6 | 2.1 | 0.1 |

Since a solid agricultural chemicals composition of the present invention uses fragments of a fibre crop which is excellent in oil absorbency and excellent in environmental safety owing to its favorable biodegradability as a carrier, it satisfies the quality required for a solid agricultural chemicals composition. That is, the carrier is high in oil absorbency, which enables to contain an agricultural chemicals ingredient in high concentration. Moreover, the agrochemically active ingredient in the chemicals formulation does not easily powder, nor easily seep out. Furthermore, since the agrochemically active ingredient is not released so soon, making the composition residual-effective and, at the same time, since the carrier is biodegradability, it is released completely after a lapse of a predetermined time, and has no fear of remaining in the soil.

Still further, since a fragment of a fibre crop has some drift, when a solid agricultural chemicals composition of the present invention is used as a granule type formulation or a jumbo type formulation to be directly thrown in a paddy field, it spreads over on the surface of water while drifting, and the concentration of the agricultural chemicals ingredient at the point of application does not become high, so that it has an effect to spread the agrochemically active ingredient uniformly over the whole paddy field in a short time. Further, weight of one granulate containing the agrochemically active ingredient in high concentration is heavy and the granule is safe without drifting of the chemicals formulation even when it is applied in the air, and enables labor-saving prevention of breeding and extermination of weeds, insects and so forth, since the granule spreads over the surface of water even when it is applied to a limited area.

Further, since a fragment of a fibre crop is combustible, when a solid agricultural chemicals composition of the present invention is used as a smoking agent, it can be used as that of not containing nitrocellulose by using this fragment as a burning agent and combining it with a suitable forming agent and combustion regulator.

What is claimed is:

1. A solid composition, comprising:

fragments of a fiber crop having high oil absorbency and one or more agricultural chemicals, wherein at least one of the agricultural chemicals is a liquid at room temperature or a solution or dispersion in a liquid solvent, the oil absorption capacity of said fragments is 100 or more, and the agricultural chemicals or the dispersed or dissolved agricultural chemicals are oils.

2. The solid composition according to claim 1, wherein at least one of the agricultural chemicals is liquid at room temperature.

3. The solid composition according to claim 1, wherein the fragments are obtained by chopping, crushing or pulverizing the fiber crop.

4. The solid composition according to claim 1, wherein the fragments are derived from crushed trunk fragment of kenaf of the genus Confederate rose in the Hollyhock family.

5. The solid composition according to claim 4, wherein the genus Confederate rose in the Hollyhock family is *Hibiscus cannabinus* Linn. or *Hibiscus Sabdariffa* Linn.

6. The solid composition according to claim 1, wherein the solid composition comprises 1 to 95 parts by weight of fragments of fiber crop and 0.1 to 70 parts by weight of the agricultural chemicals.

7. The solid composition according to claim 1, wherein the solid composition is wrapped with a water-soluble film or a water-dispersible film.

8. The solid composition according to claim 7, wherein the water-soluble film comprises a polyvinyl alcohol.

9. A method of preparing the solid agricultural composition of claim 1, comprising:

impregnating fragments of a fiber crop having high oil absorbency with one or more agricultural chemicals, wherein at least one of the agricultural chemicals is a liquid at room temperature or a solution or dispersion in a liquid solvent; and then making the impregnated fragments into a shape of powder, granule or tablet.

10. The method according to claim 9, further comprising:

wrapping the solid agricultural composition with a water-soluble film.

11. The solid composition according to claim 1, wherein at least one of the agricultural chemicals is a solution or dispersion in a liquid solvent.

12. The composition of claim 1, wherein the solid composition is in the form of a powder or granulate and the particle size of the fragments is 0.2 mm or less.

13. The composition of claim 1, wherein the particle size of the fragments is 0.2 mm or less.

14. The composition of claim 1, wherein the particle size of the fragments is 0.05 mm or less.

15. A method, comprising:

applying the solid composition according to claim 1 into a submerged paddy field, a farm, a facility, or a non-cultivated area.

16. The method of claim 15, wherein the solid composition is wrapped with a water-soluble film or a water-dispersible film.

* * * * *